(12) United States Patent
Guggino et al.

(10) Patent No.: US 8,664,237 B2
(45) Date of Patent: Mar. 4, 2014

(54) SPIPERONE DERIVATIVES AND METHODS OF TREATING DISORDERS

(75) Inventors: William B. Guggino, Baltimore, MD (US); Erik M. Schwiebert, Birmingham, AL (US); Lihua Liang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 204 days.

(21) Appl. No.: 13/122,537

(22) PCT Filed: Oct. 1, 2009

(86) PCT No.: PCT/US2009/005441
§ 371 (c)(1),
(2), (4) Date: Oct. 18, 2011

(87) PCT Pub. No.: WO2010/039260
PCT Pub. Date: Apr. 8, 2010

(65) Prior Publication Data
US 2012/0029005 A1    Feb. 2, 2012

Related U.S. Application Data

(60) Provisional application No. 61/102,135, filed on Oct. 2, 2008.

(51) Int. Cl.
*A61K 31/438* (2006.01)

(52) U.S. Cl.
USPC .......................................................... 514/278

(58) Field of Classification Search
USPC .......................................................... 514/278
See application file for complete search history.

(56) References Cited

PUBLICATIONS

Poulain et al., "From Hit to Lead. Analyzing Structure-Profile Relationship", Journal of Medicinal Chemistry, 2001, 44, pp. 3391-3401.
Monnet, "Functional Cooperation Between Neurosteroids and D2 Dopamine Antagonist on CK1-Evoked [3H] Noradrenaline Release: Modulation by Calcium Channel Blocker", Journal of Neuroendocrinology, 2002, 14, pp. 955-962.
Mestikawy et al., "Pharmacological and Biochemical Characterization of Rat Hippcampal 5-Hydroxytryptamine 1A Receptors Solubilized by 3-[3-(Cholamidopropyl)dimethylammonio]-1-Propan Sulfonate (CHAPS)", Journal of Neurochemistry, 1988, 51(4), pp. 1031-1040.

*Primary Examiner* — Jennifer M Kim
(74) *Attorney, Agent, or Firm* — Johns Hopkins Technology Transfer

(57) ABSTRACT

Described herein are spiperone derivative compounds which have been found to be useful in methods of stimulating CaCC and treating disorders (or symptoms thereof) associated with CaCC including cystic fibrosis, wherein a compound of the invention is administered to a subject.

1 Claim, 24 Drawing Sheets

FIG. 8

SPIPERONE ACTIVATES CACC IN THE AIRWAY

Table 1. *Ringer Solutions*

Solutions Used in In Vitro Experiment

| | NMDG, mM | NaCl, mM | KCl, mM | CaCl$_2$, mM | EGTA, mM | HEPES, mM | MgCl$_2$, mM | pH |
|---|---|---|---|---|---|---|---|---|
| ECaT Ringer solution | 140 | | 5 | 3 | | 10 | | 7.9 |
| Ca$^{2+}$-free ECaT Ringer solution | 140 | | 5 | | 1 | 10 | | 7.9 |
| Normal Ringer solution | | 140 | 5 | 1.5 | | 10 | 1 | 7.3 |
| Ca$^{2+}$-free normal Ringer solution | | 140 | 5 | | 1 | 10 | 1 | 7.3 |

Solutions Used in In Vivo Experiment

| | NaCl, mM | Na gluconate, mM | CaCl$_2$, mM | Ca gluconate, mM | MgCl$_2$, mM | MgSO$_4$, mM | K$_2$HPO$_4$, mM | KH$_2$PO$_4$, mM | Amiloride, μM | pH |
|---|---|---|---|---|---|---|---|---|---|---|
| Baseline Ringer Solution | 135 | | 2.25 | | 1.2 | | 2.4 | 0.4 | | 7.4 |
| Baseline Ringer Solution + amiloride | 135 | | 2.25 | | 1.2 | | 2.4 | 0.4 | 100 | 7.4 |
| O-Cl- baseline Ringer Solution | | 135 | | 2.2 | | 1.2 | 2.4 | 0.4 | 100 | 7.4 |

ECaT, enhanced Ca$^{2+}$ transfer; NMDG, *N*-methyl-D-glucamine

*Compounds with $EC_{50} < 50 \mu M$*

| Compounds | Class | $EC_{50}, \mu M$ |
|---|---|---|
| Pyrithione zinc | Antibacterial | 14 |
| Spiperone | Antipsychotic | 9.3 |
| Phenylmercuric acetate | Antibacterial | 20 |
| Tomatine | Alkaloid | 15 |
| Hexachlorophene | Antibacterial | 20 |
| Thiram | Antibacterial | 10.6 |
| Bepridil hydrochloride | $Na^+/Ca^{2+}$ exchanger blocker | 25.5 |
| 5-(N,N-hexamethylene) amiloride | $Na^+/H^+$ exchanger inhibitor | 11.6 |

SPIPERONE DERIVATIVES AND METHODS OF TREATING DISORDERS

RELATED APPLICATIONS

This application is a 35 U.S.C. §371 U.S. national entry of International Application PCT/US2009/005441 (WO 2010/039260) having an International filing date of Oct. 1, 2009 which claims the benefit of U.S. Provisional Application No. 61/102,135, filed Oct. 2, 2008. The entire contents of which are incorporated herein by this reference.

BACKGROUND OF THE INVENTION

Cystic fibrosis (CF) is the most common genetic disease in Caucasian populations, with an incidence of 1 in 2,000 live births and a carrier frequency of approximately 1 in 20. It is inherited as an autosomal recessive disease. The cystic fibrosis gene has been mapped, cloned, and sequenced (Ronimens et al., Science 245:1059-1065 (1989); Kerem et al., Science 245:1073-1080 (1989)). The gene product is the cystic fibrosis transmembrane regulator (CFTR) which functions as a chloride ion channel in the apical membranes of secretory epithelial cells (Anderson et al., Science 251:679-682 (1991)). The expression of the CFTR is most prominent in sweat glands and the respiratory and gastrointestinal tracts (Collins, F. S., Science 256:774-779 (1992)). CF is a disease of the epithelial cells, and the distribution of CFTR is essentially consistent with the clinical pathology.

Cystic fibrosis (CF) is caused by any one of a thousand mutations that affect the cystic fibrosis transmembrane conductance regulator gene (CFTR). CFTR produces chloride ($Cl^-$) channels that are regulated by cAMP. These channels are expressed in many cellular epithelia including the lung, pancreas, intestine, hepatobiliary tract, sweat gland, and vas deferens (Sheppard, D N and Welsh M J. *Physiol Rev* 79: S23-S45, 1999). The CFTR gene was cloned in 1989 (Riordan J R, et al. *Science* 245: 1066-1073, 1989).

In CF, the functionally defective apical membrane chloride channel secondarily leads to a loss of luminal sodium and water. In airways, the increase in sodium absorption and reduction in chloride secretion both lead to a loss of airway surface water. Thus, airway mucus is thickened because of insufficient endobronchial water. Bronchiolar plugging and decreased mucociliary clearance follow. These changes in the pulmonary environment result in an increase in bacterial colonization. The colonization of the lung leads to a cycle of inflammation, destruction, and further colonization. The microorganisms colonizing the lungs attract neutrophils which contain and resolve a pulmonary infection in the normal host. However, in the patient with CF, the release of proteolytic enzymes by neutrophils further damages lung parenchyma. Neutrophils release neutrophil elastase which causes many typical pathologic features of CF, including epithelial damage, bronchial gland hyperplasia (leading to increased mucus production), and connective tissue damage resulting in bronchial distortion (Stockley et al., Clin. Sci. 74:645-650 (1988)). Neutrophils also release serine protease, a factor that damages bronchial cilia (Cole, P. J., Eur. J. Respir. Dis. 69(suppl 147):6-15 (1986)). The damaged bronchial cilia have decreased ciliary beat frequency and a reduction in mucociliary clearance. In the normal host, neutrophil proteases are controlled by the naturally occurring protease inhibitors found in the pulmonary tree. The most potent of these, alpha-1-antitrypsin, irreversibly binds with high affinity to serine protease. However, in the lung of the patient with CF, proteases are produced by a variety of cells besides neutrophils, including pulmonary macrophages and the microorganism, *Pseudoinonas aeruginosa* (Fick et al., Chest 95:215S-216S (1989)). This excessive protease production overwhelms the naturally occurring endogenous protease inhibitors.

As a result of these physiological changes, respiratory tract diseases are responsible for more than 90% of the morbidity and mortality in CF (Hata et al., Clin. Chest Med. 9:679-689 (1988)).

In the airway, defective CFTR impairs $Cl^-$ secretion from epithelial cells and increases their sodium ($Na^+$) absorption. This changes the normal ion composition and dehydrates the airway surface liquid (ASL), thus decreasing its volume. Airway mucus becomes thick and is poorly cleared from the lungs, which enables bacteria to colonize the area. Eventually respiration fails (Verkman A S, Song Y and Thiagarajah J R. *Am J Physiol Cell Physiol* 284: C2-15, 2003).

There has been considerable work to repair CFTR's $Cl^-$ ion transit deficiency, but rescue has not been practical so far. For example, the most common CFTR mutation $\Delta$F508-CFTR is amenable to rescue at 27° C., but that temperature is too low for the human body. Some chemicals have shown that they can rescue CFTR, and the best are under Phase I or Phase II clinical trials.

Several non-CFTR chloride channels have been identified in airway cells including the family of voltage-dependent $Cl^-$ channels, volume-regulated anion channels (VRAC), and, calcium ($Ca^{2+}$)-activated $Cl^-$ channels (CaCCs) (Nilius B and Droogmans G. *Acta Physiol Scand* 177: 119-147, 2003; Verkman A S, Song Y and Thiagarajah J R. *Am J Physiol Cell Physiol* 284: C2-15, 2003). Previous studies have shown that CaCCs are present in the apical membrane of both normal and CF airway epithelia (Anderson M P and Welsh M J. *Proc Natl Acad Sci USA* 88: 6003-6007, 1991). Even in CF, $Ca^{2+}$-activated $Cl^-$ secretion is intact and provides a therapeutic target to circumvent the $Cl^-$ secretion defect in CF (Nilius B and Droogmans G. *Acta Physiol Scand* 177: 119-147, 2003). Denufosol and Moli1901, which stimulate CaCC and target this therapeutic pathway, are currently being evaluated in clinical trials. Denufosol, a chemically stable $P2Y_2$ receptor agonist, was shown to increase chloride and fluid secretion in preclinical studies (Kellerman D, et al. *Pulm Pharmacol Ther* 21: 600-607, 2008). It improved the lung function by 2.5% in a 24 week treatment in a phase III trial (Storey S and Wald G. *Nat Rev Drug Discov* 7: 555-556, 2008). Moli1901 (formerly known as Duramycin) is a stable polypeptide. In a phase I trial, Moli1901 stimulated $Cl^-$ transport in normal and CF epithelia (Zeitlin P L et al. *Chest* 125: 143-149, 2004). 4 weeks of treatment with aerosolized Moli1901 caused a 2% increase in lung function (Storey S and Wald G. *Nat Rev Drug Discov* 7: 555-556, 2008). Although these two agents are being studied intensively, the discovery of more compounds to activate this pathway without any adverse effects would still be beneficial for the potential treatment of CF.

High-throughput screening allows assessment of a large number of compounds quickly, and has been used widely in drug discovery in recent years (Monteith G R and Bird G S. *Trends Pharmacol Sci* 26: 218-223, 2005). A goal was to search the 2000 compounds of MicroSource Discovery's MSSP library for compounds that would enhance cytoplasmic $Ca^{2+}$, which in turn would activate the CaCCs and alleviate the defective $Cl^-$ secretion in CF airways without adverse side effects.

It has been previously disclosed that zinc with ATP or zinc alone reliably causes a sustained increase in cytoplasmic $Ca^{2+}$ in cells bathed in a Ringer's solution modified to enhance $Ca^{2+}$ transfer (ECaT Ringer's see Table 1). Both zinc and ATP activate P2X purinergic receptors that are non-selective cation channels expressed in human airway surface epithelia (Liang L, et al. *Am J Physiol Cell Physiol* 289: C388-C396, 2005; Zsembery A, et al. *J Biol Chem* 278: 13398-13408, 2003; Zsembery A, et al. *J Biol Chem* 279: 10720-10729, 2004). The resulting increase in cytoplasmic $Ca^{2+}$ then translates into sustained $Cl^-$ secretion in both CF and non-CF airway epithelia in vivo and in vitro. Zinc, however, is a biometal, so the amount of it taken into the body would be a concern in CF therapy.

SUMMARY OF THE INVENTION

In one aspect, the invention provides a method of treating a disease or disorder associated with calcium-activated chlorine channels (CaCC) in a subject, the method comprising the step of administering to the subject an effective amount of a compound of formula I:

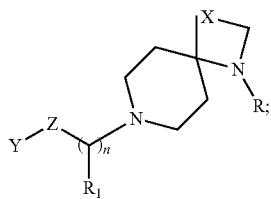

or a pharmaceutically acceptable salt thereof,
wherein,
X is O, S, NR', C(O)NR', NR'C(O), SO, or $SO_2$;
each R' is independently H, optionally substituted alkyl, or optionally substituted aryl;
R is H, optionally substituted alkyl, or optionally substituted aryl;
each $R_1$ is independently H, alkyl, alkenyl, alkynyl, cycloalkyl, heterocycloalkyl, aryl, or heteroaryl, each of which may be optionally substituted;
Z is absent, $CH_2$, $CHR_1$, C(O), C(O)O, C(O)NH, C(O)$NR_1$, C(O)$CH_2$, C(O)O$CH_2$, C(O)NH$CH_2$, or C(O)$NR_1CH_2$;
Y is an optionally substituted alkyl, or

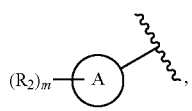

wherein
ring A is an optionally substituted cycloalkyl, optionally substituted heterocycloalkyl, optionally substituted aryl, or optionally substituted heteroaryl;
each $R_2$ is independently halogen, nitro, cyano, NR"R", NHR", OR", SR", optionally substituted alkyl, optionally substituted aryl,
each R" is independently H, an optionally substituted alkyl, an optionally substituted aryl, an optionally substituted aralkyl, an optionally substituted heteroaryl, or optionally substituted heterocyclic;
m is 0, 1, 2, 3, or 4; and
n is 0, 1, 2, 3, or 4.

In another aspect, the invention provides a method of treating a disease or disorder associated with calcium-activated chlorine channels (CaCC) in a subject, wherein the subject is identified as being in need of a CaCC stimulation, the method comprising the step of administering to the subject an effective amount of a compound of formula I:

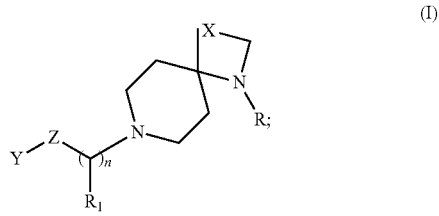

or a pharmaceutically acceptable salt thereof,
wherein,
X is O, S, NR', C(O)NR', NR'C(O), SO, or $SO_2$;
each R' is independently H, optionally substituted alkyl, or optionally substituted aryl;
R is H, optionally substituted alkyl, or optionally substituted aryl;
each $R_1$ is independently H, alkyl, alkenyl, alkynyl, cycloalkyl, heterocycloalkyl, aryl, or heteroaryl, each of which may be optionally substituted;
Z is absent, $CH_2$, $CHR_1$, C(O), C(O)O, C(O)NH, or C(O)$NR_1$;
Y is an optionally substituted alkyl, or

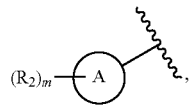

wherein
ring A is an optionally substituted cycloalkyl, optionally substituted heterocycloalkyl, optionally substituted aryl, or optionally substituted heteroaryl;
each $R_2$ is independently halogen, nitro, cyano, NR"R", NHR", OR", SR", optionally substituted alkyl, optionally substituted aryl,
each R" is independently H, an optionally substituted alkyl, an optionally substituted aryl, an optionally substituted aralkyl, an optionally substituted heteroaryl, or optionally substituted heterocyclic;
m is 0, 1, 2, 3, or 4; and
n is 0, 1, 2, 3, or 4.

In another aspect, the invention provides a method of modulating CaCC in a subject, the method comprising the step of administering to the subject an effective amount of a compound of formula I.

In another aspect, the invention provides a method of modulating CaCC in a subject, the method comprising the step of administering to the subject an effective amount of a compound identified in a screening assay.

In another aspect, the invention provides a method of treating Cystic Fibrosis in a subject, the method comprising the step of administering to the subject an effective amount of a compound of formula I.

In another aspect, the invention provides a method for increasing the amount of airway surface water in the lungs of a subject, the method comprising: administering a compound of formula I to the subject, wherein the compound activates the calcium-dependent chloride channel.

In another aspect, the invention provides a method for increasing the amount of airway surface water in the lungs of a subject having a disease characterized by a cystic fibrosis transmembrane regulator having decreased activity compared to normal cystic fibrosis transmembrane regulator, the method comprising: administering a compound of formula I to the subject having the disease, wherein the compound activates the calcium-dependent chloride channel.

In another aspect, the invention provides a method for increasing ciliary activity in the lungs of a subject having reduced ciliary activity wherein the reduced ciliary activity is caused, in part, by having a cystic fibrosis transmembrane regulator having decreased activity compared to normal cystic fibrosis transmembrane regulator, the method comprising: administering a compound of formula I to the subject having the reduced ciliary activity, wherein the compound activates the calcium-dependent chloride channel.

In other aspects, the invention provides a method for increasing ciliary activity in the lungs of a subject having reduced ciliary activity wherein the reduced ciliary activity results from a decrease in the amount of chloride being secreted from bronchial epithelial cells, the method comprising: administering a compound of formula I to the subject having said reduced ciliary activity.

In certain aspects, the invention provides a method for increasing chloride secretion from bronchial epithelial cells in the lungs of a subject having reduced chloride secretion from bronchial epithelial cells, the method comprising: administering a compound of formula I that activates the calcium-dependent chloride channel to the subject having reduced chloride secretion.

In another aspect, the invention provides a method for increasing chloride secretion from cells in a subject having a disease characterized by having reduced chloride secretion from cells, the method comprising: administering a compound of formula I, to the subject having the disease.

The invention also provides the use of a compound in the manufacture of a medicament for stimulating CaCC in a patient, wherein the compound is a compound of formula I.

In another aspect, the invention provides a pharmaceutical composition comprising a compound of formula I and a pharmaceutically suitable excipient.

In certain aspects, the invention provides a kit comprising an effective amount of a compound of formula I in unit dosage form, together with instructions for administering the compound to a subject suffering from or susceptible to a CaCC related disease.

BRIEF DESCRIPTION OF THE DRAWINGS

FIG. 8 shows the ringer solutions that are used for this study.

DETAILED DESCRIPTION OF THE INVENTION

I. Definitions

Figure 1:
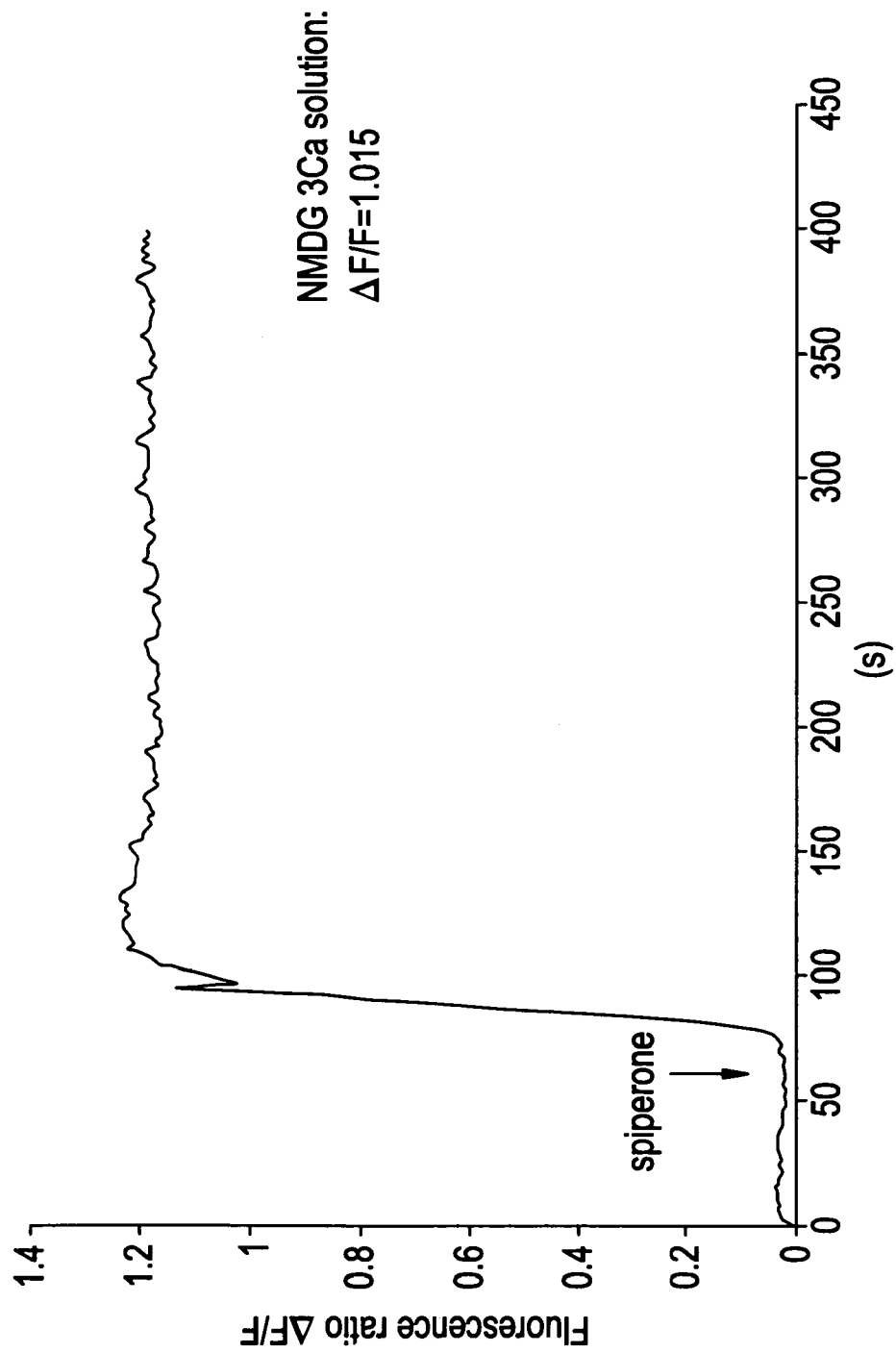
FIG. 1 shows that spiperone stimulates a sustained calcium increase in N-methyl-D-Glucamine solution (NMDG 140 mM, KCl 5 mM, $CaCl_2$ 3 mM, Hepes 10 mM, pH=7.9).
Figure 2:
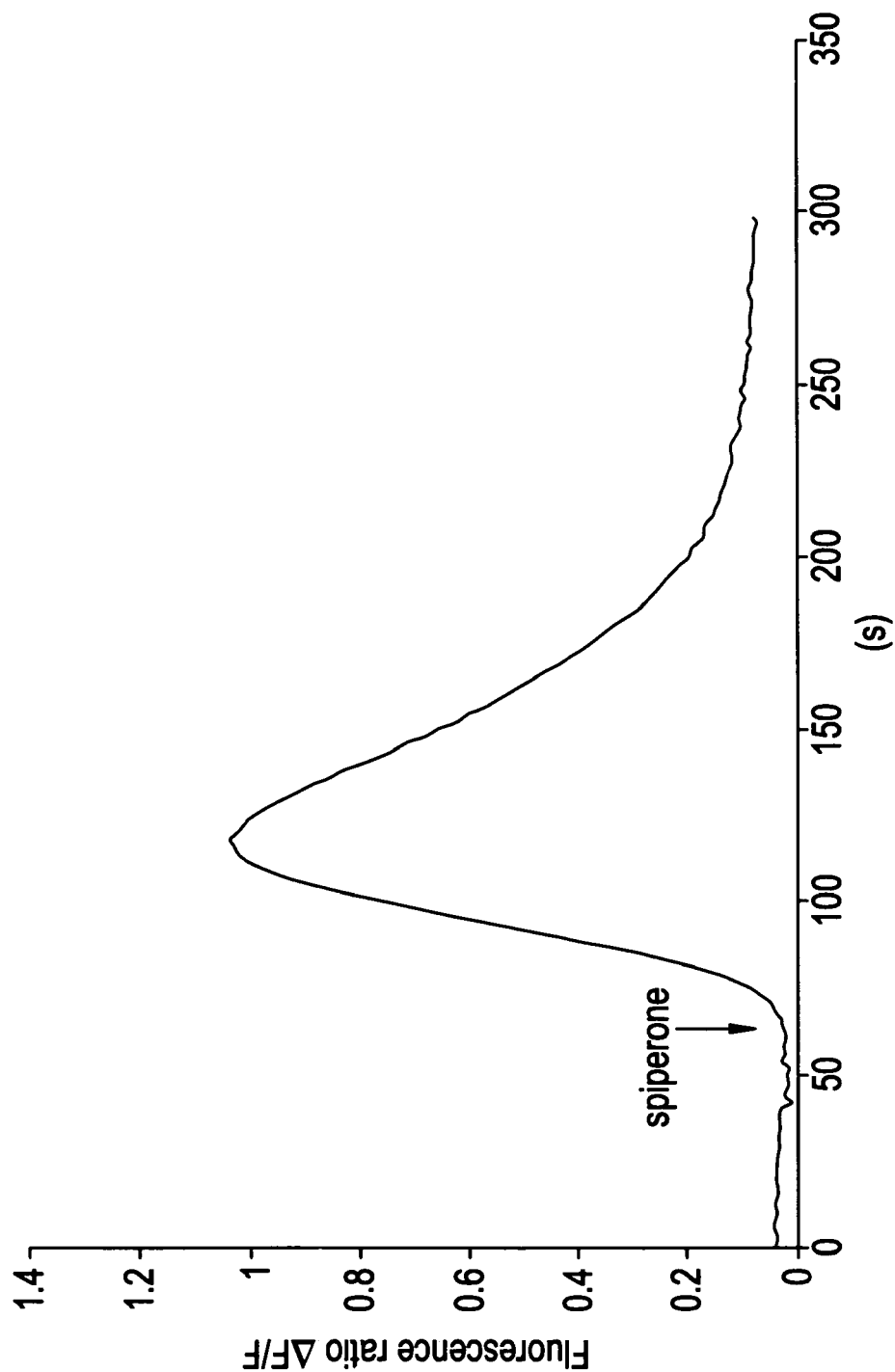
FIG. 2 shows that spiperone stimulates a transient calcium increase in normal ringer solution (NaCl 140 mM, KCl 5 mM, $CaCl_2$ 1.5 mM, $MgCl_2$ 1 mM, and Hepes 10 mM, pH 7.3).
Figure 3:
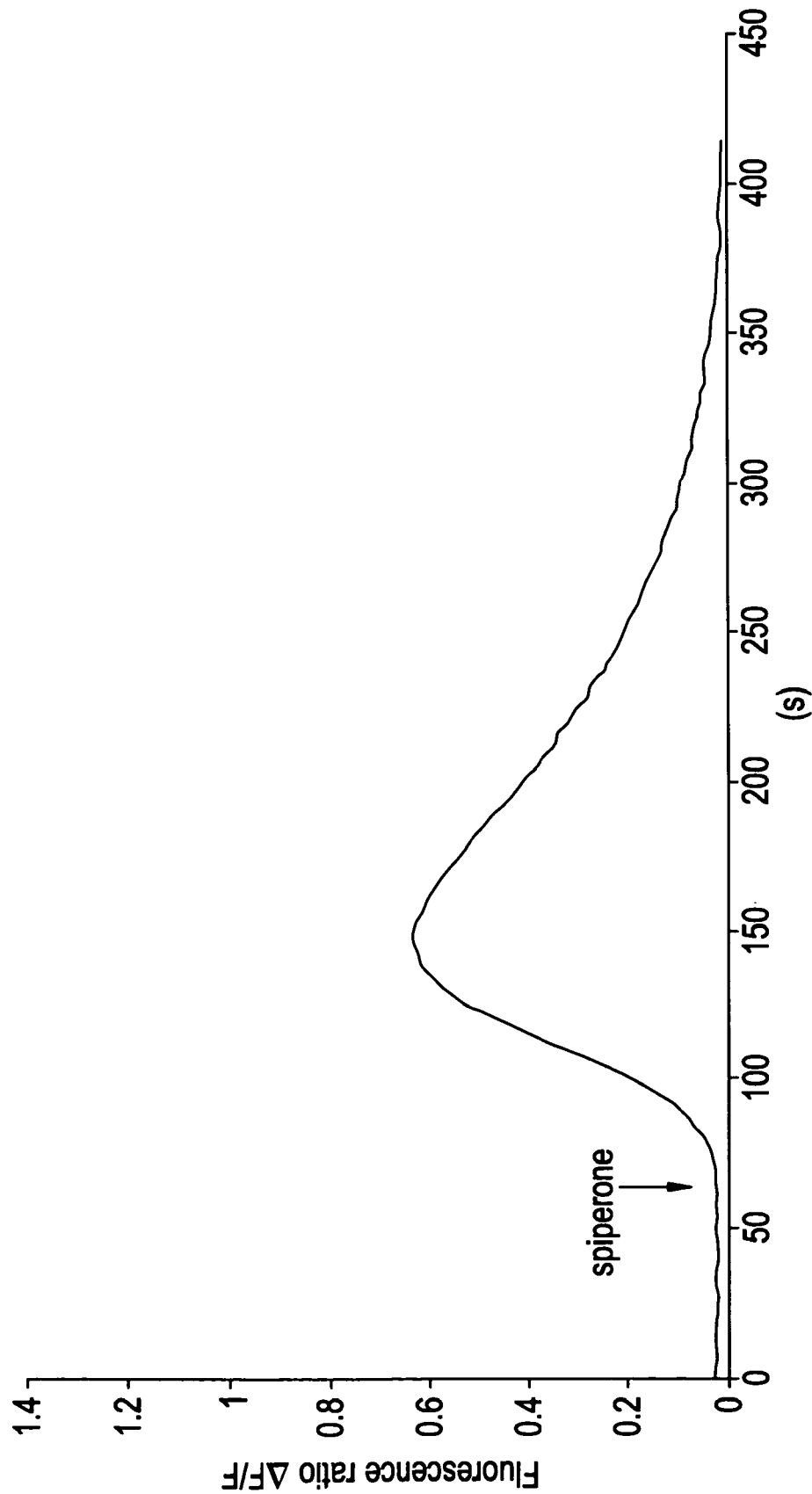
FIG. 3 shows that spiperone stimulates a transient calcium increase in the absence of extracellular calcium solution (NaCl 140 mM, KCl 5 mM, EGTA 1 mM, and Hepes 10 mM, pH 7.3).
Figure 4:
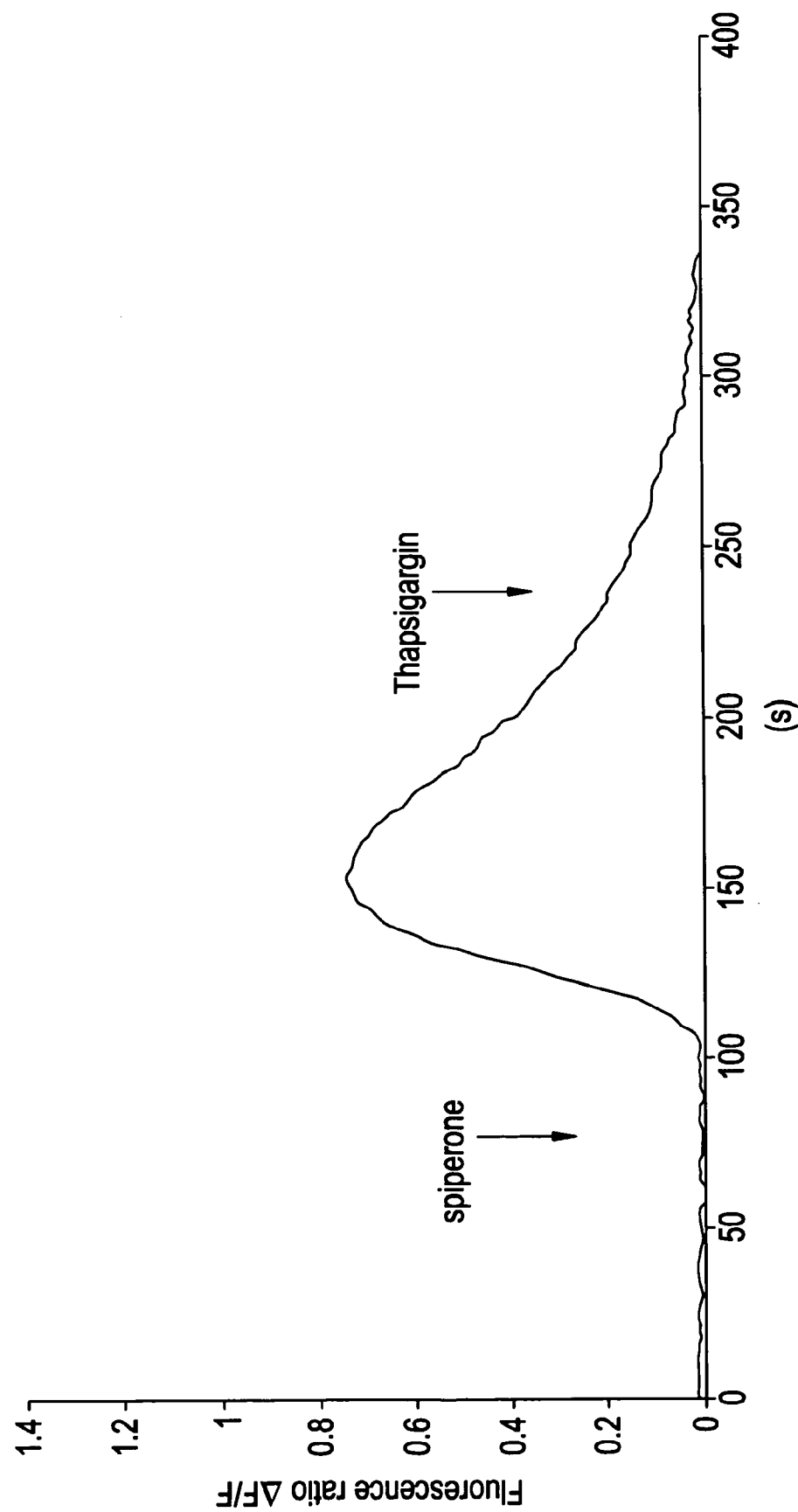
FIG. 4 shows that thapsigargin cannot release calcium from the ER after spiperone stimulation, indicating that spiperone releases calcium from the ER.
Figure 5:
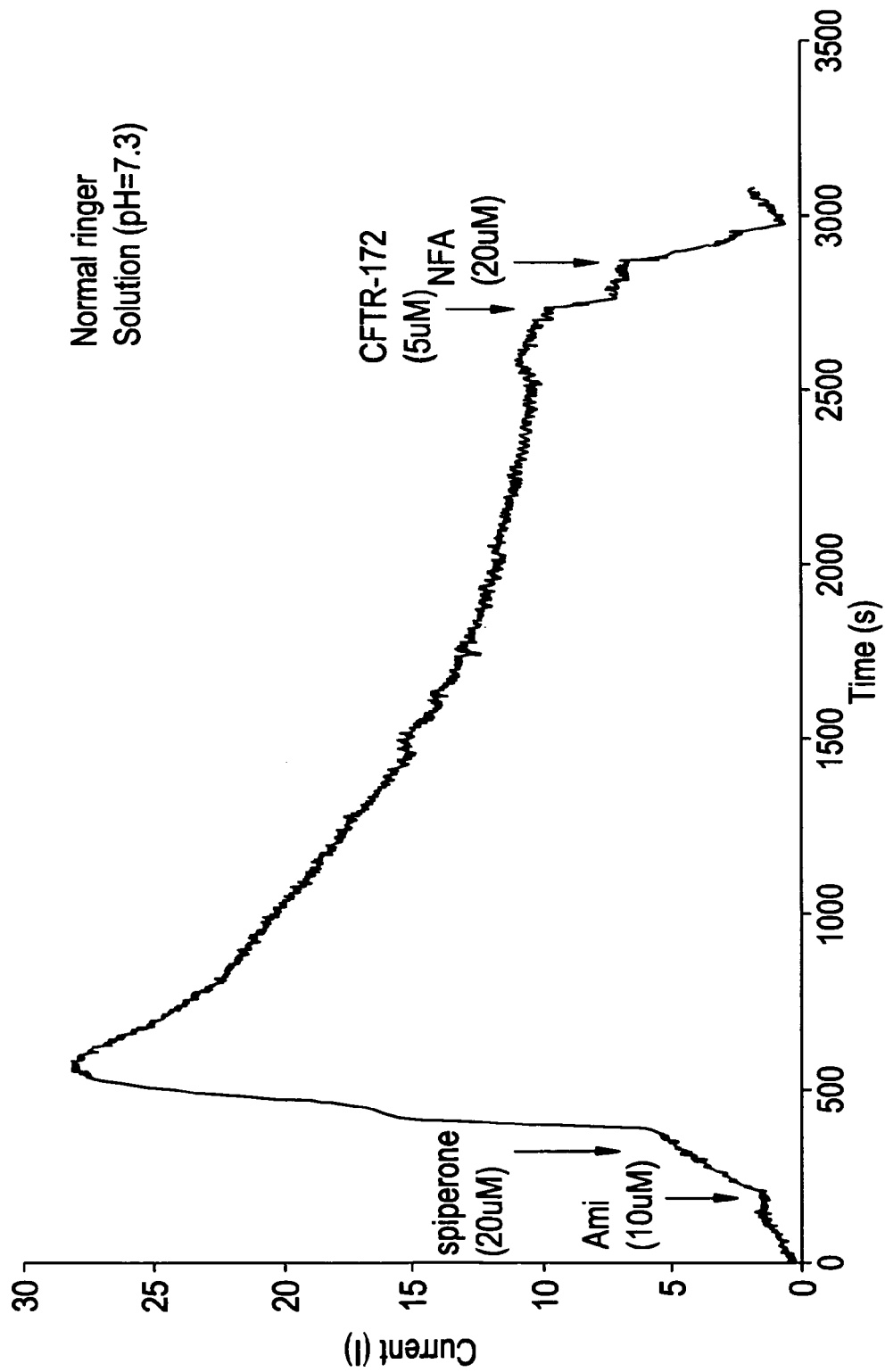
FIG. 5 shows that spiperone stimulates chloride secretion in the presence of sodium absorption blocker amiloride in Calu-3 cells.
Figure 6:
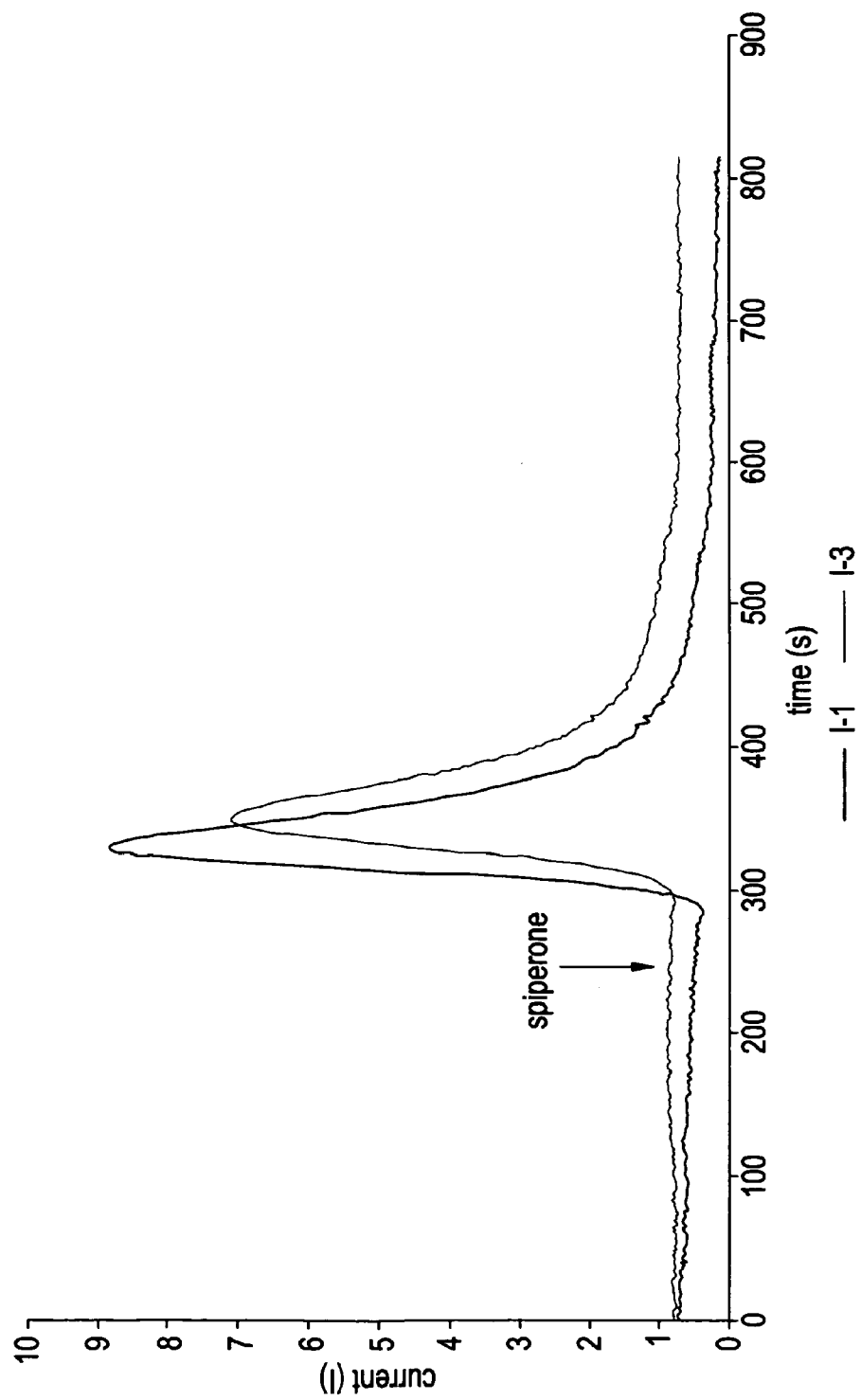
FIG. 6 shows the spiperone stimulates chloride secretion in CFBE41o-cells.
Figure 7:
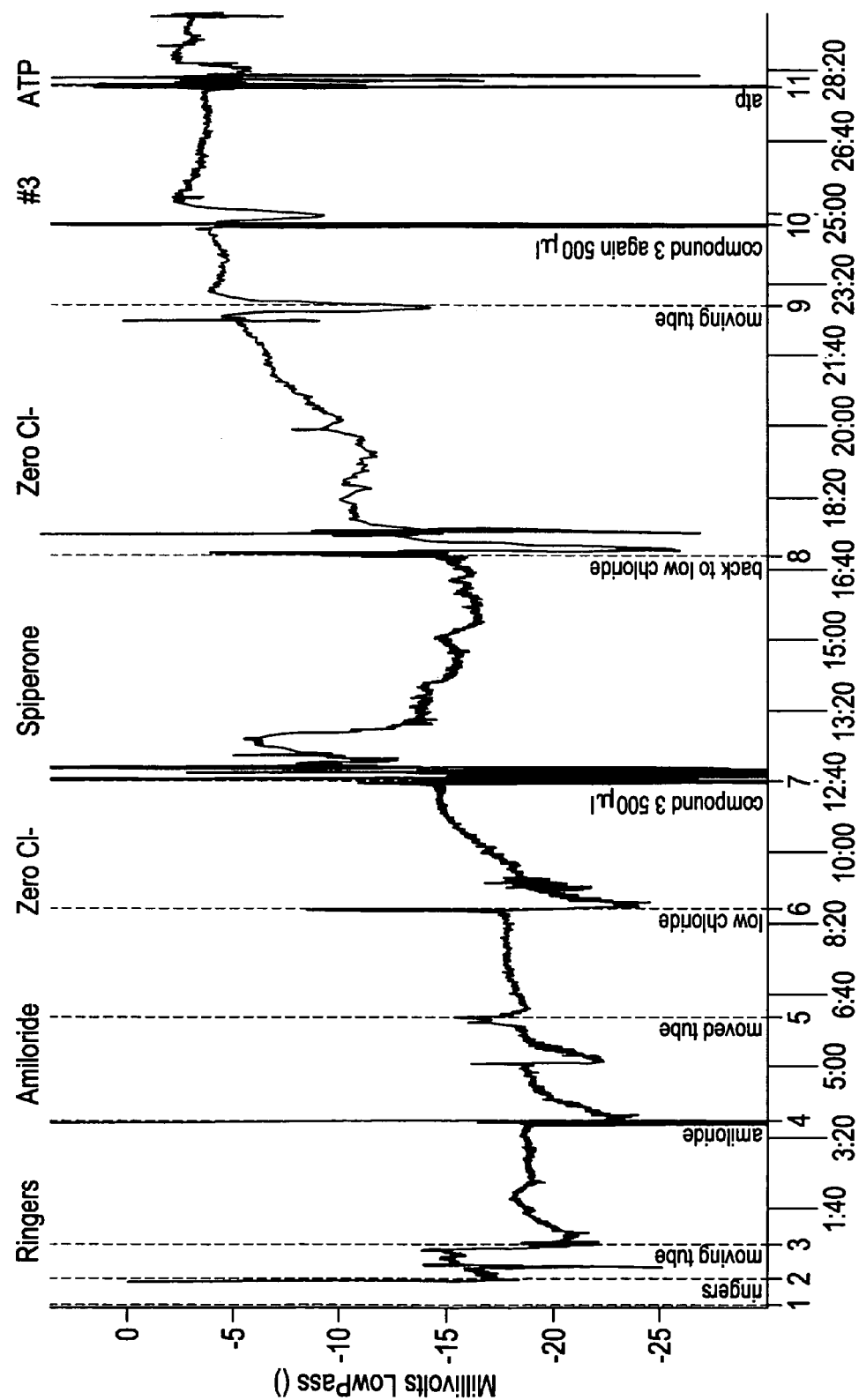
FIG. 7 shows that spiperone stimulates chloride secretion in CFTR knock out mouse nasal epithelia.
Figure 9A:
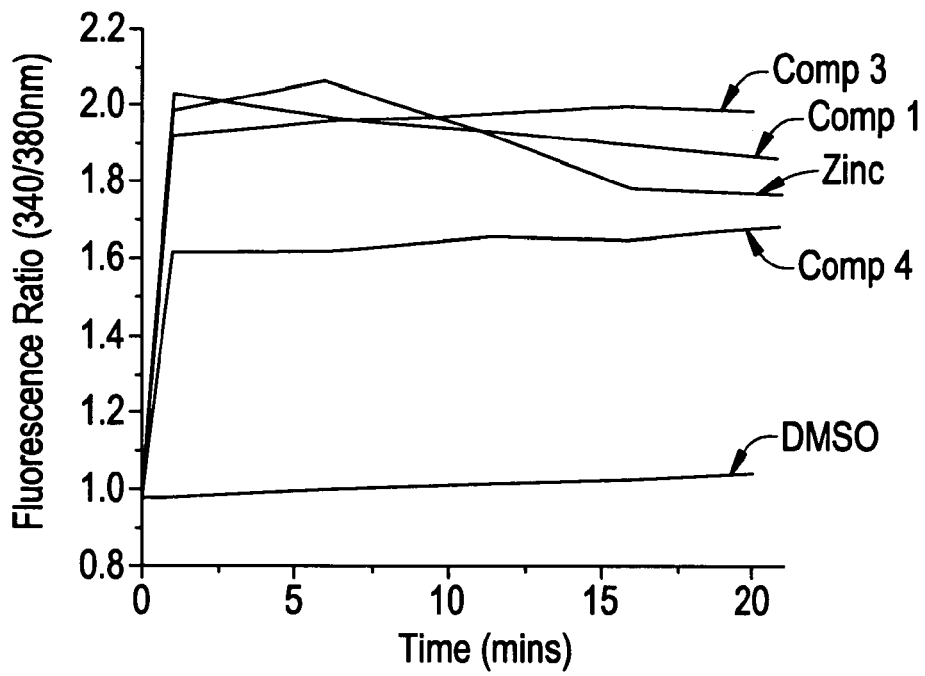
FIG. 9 shows the change in fluorescence ratio for three sample hits compared to zinc and 5% DMSO and dose response curve for spiperone, zinc and compound two hits
Figure 9B:
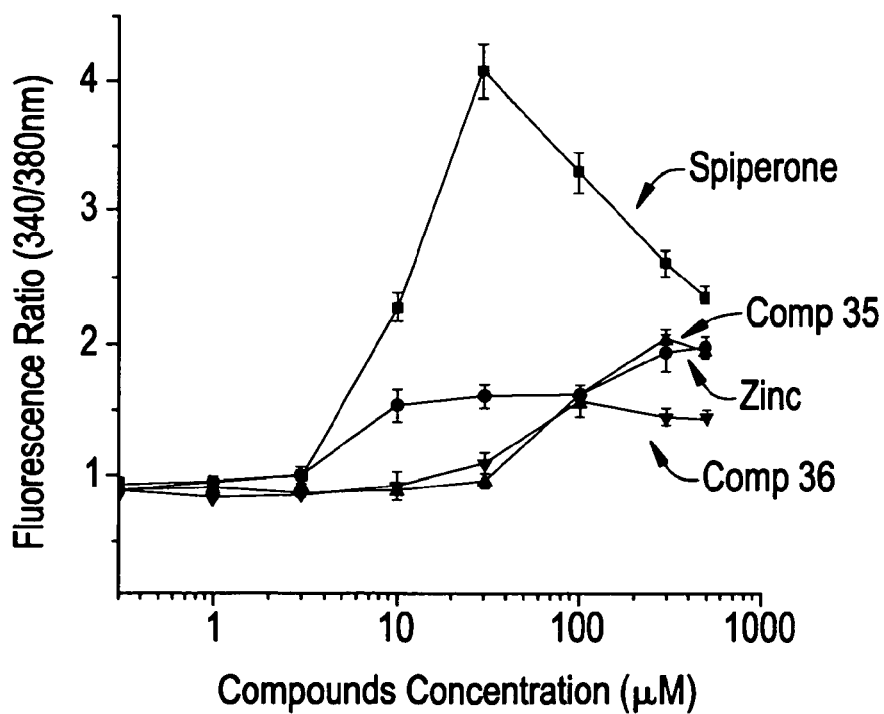

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of alkyl radicals include, but are not limited to, methyl, ethyl, propyl, isopropyl, n-butyl, tert-butyl, neopentyl, n-hexyl heptyl, octyl radicals.

The term "alkenyl," as used herein, denote a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denote a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "cycloalkyl" or "carbocyclic" are used interchangeably, and as used herein, denotes a monovalent group derived from a monocyclic or polycyclic saturated carbocyclic ring compound. Examples include, but are not limited to, cyclopropyl, cyclobutyl, cyclopentyl, cyclohexyl, cyclopentyl and cyclooctyl; bicyclo[2.2.1]heptyl, and bicyclo[2.2.2]octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "aryl," as used herein, refers to a mono- or polycyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl," "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH -aryl, —NH-heteroaryl, —NH-heterocycloalkyl, -dialkylamino, -diarylamino, -dihetero arylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_2$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$—heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The terms "hal," "halo" and "halogen," are used interchangeably, and as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "effective amount" is used throughout the specification to describe concentrations or amounts of compounds according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated.

As used herein, the terms "prevent," "preventing," "prevention," and the like refer to reducing the probability of developing a disorder or condition in a subject, who does not have, but is at risk of or susceptible to developing a disorder or condition.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the term "Cystic Fibrosis" refers to a genetic disorder that causes mucus in the body to become thick, typically in the lungs and pancreas. People who have cystic fibrosis can have serious breathing problems and lung disease. They can also have problems with nutrition, digestion, growth, and development.

II. Compounds Utilized in the Invention

Certain compounds of the present invention may exist in particular geometric, isomeric, or stereoisomeric forms. The present invention contemplates all such compounds, including cis- and trans-isomers, R- and S-enantiomers, racemates and racemic mixtures, single enantiomers, individual diastereomers, diastereomeric mixtures diastereomers, (D)-isomers, (L)-isomers, the racemic mixtures thereof, and other mixtures thereof, as falling within the scope of the invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). Additional asymmetric carbon atoms may be present in a substituent such as an alkyl group. All such enriched isomers, as well as racemic mixtures thereof, are intended to be included in this invention. All such isomeric forms of such compounds are expressly included in the present invention. All crystal forms of the compounds described herein are expressly included in the present invention.

The compounds described above can be prepared by methods well known in the art, as well as by the synthetic routes disclosed in the examples below.

The chemicals used in the above-described synthetic route may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the heterocyclic compounds. In addition, various synthetic steps may be performed in an alternate sequence or order to give the desired compounds. Synthetic chemistry transformations and protecting group methodologies (protection and deprotection) useful in synthesizing applicable heterocyclic compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Correspondingly, the compounds described herein can be made according to methods known in the art, including those in the aforementioned treatises. It is recognized by one of ordinary skill that reaction conditions (e.g., temperature, reaction time, etc.) may be adjusted, which is routine for one of ordinary skill.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2nd. Ed., Wiley-VCH Publishers (1999); T. W. Greene and P. G. M. Wuts, *Protective Groups in Organic Synthesis,* 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

III. Methods of Treatment

In one aspect, the invention provides a method of treating a disease or disorder associated with calcium-activated chlorine channels (CaCC) in a subject, the method comprising the step of administering to the subject an effective amount of a compound of formula I:

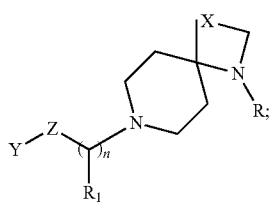

or a pharmaceutically acceptable salt thereof,
wherein,
X is O, S, NR', C(O)NR', NR'C(O), SO, or $SO_2$;
each R' is independently H, optionally substituted alkyl, or optionally substituted aryl;
R is H, optionally substituted alkyl, or optionally substituted aryl;
each $R_1$ is independently H, alkyl, alkenyl, alkynyl, cycloalkyl, heterocycloalkyl, aryl, or heteroaryl, each of which may be optionally substituted;
Z is absent, $CH_2$, $CHR_1$, C(O), C(O)O, C(O)NH, C(O)$NR_1$, C(O)$CH_2$, C(O)O$CH_2$, C(O)NH$CH_2$, or C(O)$NR_1CH_2$;
Y is an optionally substituted alkyl, or

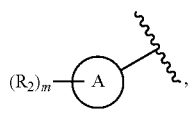

wherein
ring A is an optionally substituted cycloalkyl, optionally substituted heterocycloalkyl, optionally substituted aryl, or optionally substituted heteroaryl;
each $R_2$ is independently halogen, nitro, cyano, NR"R", NHR", OR", SR", optionally substituted alkyl, optionally substituted aryl,
each R" is independently H, an optionally substituted alkyl, an optionally substituted aryl, an optionally substituted aralkyl, an optionally substituted heteroaryl, or optionally substituted heterocyclic;

m is 0, 1, 2, 3, or 4; and
n is 0, 1, 2, 3, or 4.

In another aspect, the invention provides a method of treating a disease or disorder associated with calcium-activated chlorine channels (CaCC) in a subject, wherein the subject is identified as being in need of a CaCC stimulation, the method comprising the step of administering to the subject an effective amount of a compound of formula I:

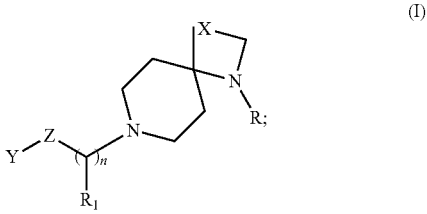

or a pharmaceutically acceptable salt thereof,
wherein,
X is O, S, NR', C(O)NR', NR'C(O), SO, or $SO_2$;
each R' is independently H, optionally substituted alkyl, or optionally substituted aryl;
R is H, optionally substituted alkyl, or optionally substituted aryl;
each $R_1$ is independently H, alkyl, alkenyl, alkynyl, cycloalkyl, heterocycloalkyl, aryl, or heteroaryl, each of which may be optionally substituted;
Z is absent, $CH_2$, $CHR_1$, C(O), C(O)O, C(O)NH, or C(O)$NR_1$;
Y is an optionally substituted alkyl, or

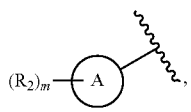

wherein
ring A is an optionally substituted cycloalkyl, optionally substituted heterocycloalkyl, optionally substituted aryl, or optionally substituted heteroaryl;
each $R_2$ is independently halogen, nitro, cyano, NR"R", NHR", OR", SR", optionally substituted alkyl, optionally substituted aryl,
each R" is independently H, an optionally substituted alkyl, an optionally substituted aryl, an optionally substituted aralkyl, an optionally substituted heteroaryl, or optionally substituted heterocyclic;
m is 0, 1, 2, 3, or 4; and
n is 0, 1, 2, 3, or 4.

In one embodiment, the disease or disorder associated with CaCC is Cystic Fibrosis, chronic bronchitis; asthma; COPD; bronchiectasis; keratoconjunctivitis sicca, Sjogren's Syndrome, general dry mouth; stripping of mucosa associated with ulcerative colitis, Crohn's disease, Dent's disease, X-linked nephrolithiasis, X-linked recessive hypophosphatemic rickets, autosomal dominant myotonia congenita, or autosomal recessive general myotonia.

In a further embodiment, the disease or disorder is Cystic Fibrosis.

In one embodiment, the compound of formula I is a compound of formula II:

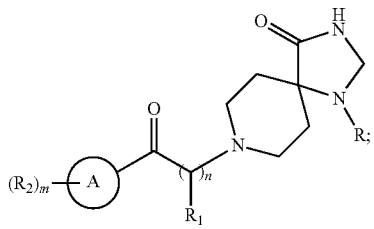
(II)

or a pharmaceutically acceptable salt thereof, wherein,

R is H, optionally substituted alkyl, or optionally substituted aryl;

each $R_1$ is independently H, alkyl, alkenyl, alkynyl, cycloalkyl, heterocycloalkyl, aryl, or heteroaryl, each of which may be optionally substituted;

ring A is an optionally substituted cycloalkyl, optionally substituted heterocycloalkyl, optionally substituted aryl, or optionally substituted heteroaryl;

each $R_2$ is independently halogen, nitro, cyano, NR"R", NHR", OR", SR", optionally substituted alkyl, optionally substituted aryl, each R" is independently H, an optionally substituted alkyl, an optionally substituted aryl, an optionally substituted aralkyl, an optionally substituted heteroaryl, or optionally substituted heterocyclic;

m is 0, 1, 2, 3, or 4; and n is 1, 2, 3, or 4.

In another embodiment, R is an optionally substituted aryl. In a further embodiment, R is phenyl or naphthyl.

In other embodiments, each $R_1$ is H.

In still another embodiment, ring A is an optionally substituted aryl, or optionally substituted heteroaryl; and each $R_2$ is independently halogen, nitro, cyano, NR"R", NHR", OR", or SR". In a further embodiment, ring A is an optionally substituted phenyl, and each $R_2$ is independently halogen, NR"R", NHR", OR", or SR".

In another embodiment, m is 1 or 2.

In certain embodiments, n is 2, 3, or 4.

In certain embodiments, p is 0 or 1.

In one embodiment, the compound is a compound of formula III:

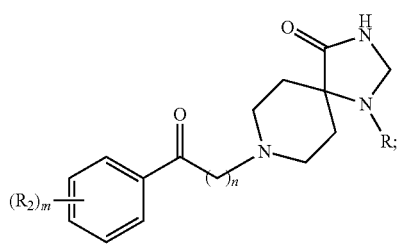
(III)

or a pharmaceutically acceptable salt thereof, wherein,

R' is H, optionally substituted alkyl, or optionally substituted aryl;

R is H, optionally substituted alkyl, or optionally substituted aryl;

each $R_2$ is independently halogen, nitro, cyano, NR"R", NHR", OR", SR", optionally substituted alkyl, optionally substituted aryl, each R" is independently H, an optionally substituted alkyl, an optionally substituted aryl, an optionally substituted aralkyl, an optionally substituted heteroaryl, or optionally substituted heterocyclic;

m is 0, 1, 2, 3, or 4; and n is 1, 2, 3, or 4.

In another embodiment, the compound is a compound of formula IV:

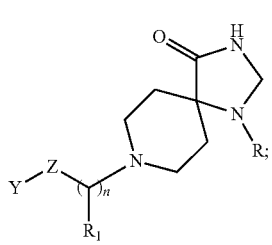
(IV)

or a pharmaceutically acceptable salt thereof, wherein,

R is H, optionally substituted alkyl, or optionally substituted aryl;

each $R_1$ is independently H, alkyl, alkenyl, alkynyl, cycloalkyl, heterocycloalkyl, aryl, or heteroaryl, each of which may be optionally substituted;

Z is absent, $CH_2$, C(O), C(O)O, C(O)$CH_2$, or C(O)O$CH_2$;

Y is an optionally substituted alkyl, or

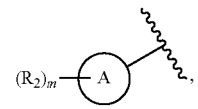

wherein ring A is an optionally substituted cycloalkyl, optionally substituted heterocycloalkyl, optionally substituted aryl, or optionally substituted heteroaryl;

each $R_2$ is independently halogen, nitro, cyano, NR"R", NHR", OR", SR", optionally substituted alkyl, optionally substituted aryl, each R" is independently H, an optionally substituted alkyl, an optionally substituted aryl, an optionally substituted aralkyl, an optionally substituted heteroaryl, or optionally substituted heterocyclic;

m is 0, 1, 2, 3, or 4; and n is 0, 1, 2, 3, or 4.

In certain embodiments, n is 1, Z is absent, and Y is

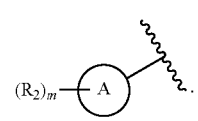

In a further embodiment, ring A is an optionally substituted phenyl or an optionally substituted benzo thiazole.

In another embodiment, n is 0, Z is C(O)CH$_2$, and Y is

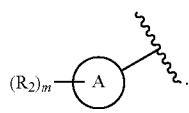

In certain embodiments, n is 0, Z is C(O)O, and Y is optionally substituted alkyl.

In certain embodiments, the compound used in the methods of the invention is

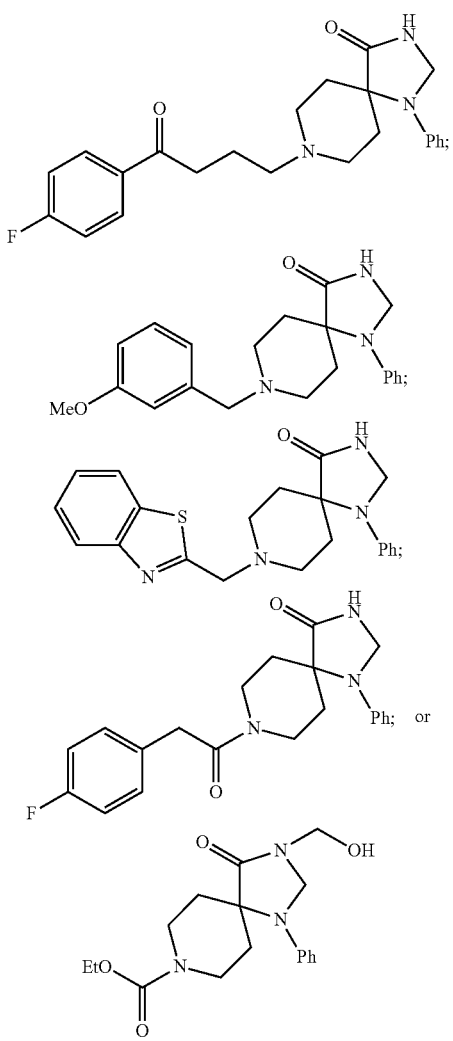

In another aspect, the invention provides a method of modulating CaCC in a subject, the method comprising the step of administering to the subject an effective amount of a compound of formula I, or any of the compounds or formulae provided herein.

In one embodiment, the modulation is stimulation.

In another aspect, the invention provides a method of modulating CaCC in a subject, the method comprising the step of administering to the subject an effective amount of a compound identified in a screening assay.

In one embodiment, the compound is a compound of formula I, or any of the compounds or formulae provided herein.

In another embodiment, the screening assay is a high throughput screening procedure.

In other embodiments, the CaCC stimulator has a IC$_{50}$ for activating CaCC greater than about 5 micromolar. In another embodiment, the CaCC stimulator has a IC$_{50}$ for activating CaCC greater than about 25 micromolar.

In another aspect, the invention provides a method of treating Cystic Fibrosis in a subject, the method comprising the step of administering to the subject an effective amount of a compound of formula I, or any of the compounds or formulae provided herein.

In one embodiment, the compound stimulates CaCC to thereby treat Cystic Fibrosis.

In another aspect, the invention provides a method for increasing the amount of airway surface water in the lungs of a subject, the method comprising: administering a compound of formula I, or any of the compounds or formulae provided herein, to the subject, wherein the compound activates the calcium-dependent chloride channel.

In another aspect, the invention provides a method for increasing the amount of airway surface water in the lungs of a subject having a disease characterized by a cystic fibrosis transmembrane regulator having decreased activity compared to normal cystic fibrosis transmembrane regulator, the method comprising: administering a compound of formula I, or any of the compounds or formulae provided herein, to the subject having the disease, wherein the compound activates the calcium-dependent chloride channel.

In another aspect, the invention provides a method for increasing ciliary activity in the lungs of a subject having reduced ciliary activity wherein the reduced ciliary activity is caused, in part, by having a cystic fibrosis transmembrane regulator having decreased activity compared to nonnal cystic fibrosis transmembrane regulator, the method comprising: administering a compound of formula I, or any of the compounds or formulae provided herein, to the subject having the reduced ciliary activity, wherein the compound activates the calcium-dependent chloride channel.

In other aspects, the invention provides a method for increasing ciliary activity in the lungs of a subject having reduced ciliary activity wherein the reduced ciliary activity results from a decrease in the amount of chloride being secreted from bronchial epithelial cells, the method comprising: administering a compound of formula I, or any of the compounds or formulae provided herein, to the subject having said reduced ciliary activity.

In certain aspects, the invention provides a method for increasing chloride secretion from bronchial epithelial cells in the lungs of a subject having reduced chloride secretion from bronchial epithelial cells, the method comprising: administering a compound of formula I, or any of the compounds or formulae provided herein, that activates the calcium-dependent chloride channel to the subject having reduced chloride secretion.

In another aspect, the invention provides a method for increasing chloride secretion from cells in a subject having a disease characterized by having reduced chloride secretion from cells, the method comprising: administering a compound of formula I, or any of the compounds or formulae provided herein, to the subject having the disease.

In certain embodiments, the invention provides a method further comprising a step of administering an additional therapeutic agent. In certain embodiments, the additional therapeutic agent is a CaCC stimulating compound. In a further embodiment, the additional therapeutic agent is an anti cystic fibrosis compound.

In certain embodiments, the step of administering the compound comprises administering the compound orally, topically, parentally, intravenously or intramuscularly.

In other embodiments, the step of administering the compound comprises administering the compound in a dosage of between about 0.1 and 120 mg/kg/day. In a further embodiment, the step of administering the compound comprises administering the compound in a dosage of less than about 500 mg/day.

In certain embodiments, the subject is a human.

The invention also provides the use of a compound in the manufacture of a medicament for stimulating CaCC in a patient, wherein the compound is a compound of formula I, or any of the compounds or formulae provided herein.

In another aspect, the invention provides a pharmaceutical composition comprising a compound of formula I, or any of the compounds or formulae provided herein and a pharmaceutically suitable excipient.

In certain aspects, the invention provides a kit comprising an effective amount of a compound of formula I, or any of the compounds or formulae provided herein, in unit dosage form, together with instructions for administering the compound to a subject suffering from or susceptible to a CaCC related disease.

The methods find use in, among other applications, the treatment of disease conditions associated with CaCC and/or respiratory system cell mucin secretion, including respiratory system cell mucin hypersecretion and respiratory system cell mucin hyposecretion. Disease conditions associated with mucin hypersecretion in the respiratory system which are amenable to treatment with the subject methods include, but are not limited to: chronic bronchitis; asthma; COPD; bronchiectasis; cystic fibrosis; keratoconjunctivitis sicca (KCS or dry eye), 'Sjogren's Syndrome', general dry mouth (a common side effect with anticholinergic drugs); stripping of mucosa associated with ulcerative colitis and Crohn's disease; and the like. Other disorders treated by the compounds of the invention include Dent's disease, X-linked nephrolithiasis, X-linked recessive hypophosphatemic rickets, autosomal dominant myotonia congenita, or autosomal recessive general myotonia.

The basic defect in CF centers around abnormal ion transport. Two ions which appear to have defective transport in the affected CF epithelial cell are sodium and chloride. In the normal epithelial cell sodium is absorbed and chloride is secreted. This movement of sodium and chloride is accompanied by the movement of water. In the affected CF epithelial cell, sodium is hyper-absorbed into the cell, taking with it water from the airways. Because chloride secretion is defective, normal chloride and water secretion into the airways is blocked. This defect in ion transport leads to a decrease in airway fluid and thickened secretions.

In the intestinal tract, three primary signal transduction mechanisms, the second messengers cAMP, cGMP or calcium, have been associated with the stimulation of epithelial chloride secretion. Activation of apical chloride secretion by either cyclic nucleotide is similar except that cAMP-dependent stimuli are generally more potent than cGMP-dependent stimuli. Cyclic nucleotides stimulate apical membrane chloride transport through the cystic fibrosis transmembrane regulator (CFTR). The calcium-dependent chloride secretory mechanisms appear to diverge and are less well defined. For example, histamine, serotonin and carbachol (an analog of acetylcholine, a critical neurohormone in the enteric nervous system) all increase intracellular calcium in intestinal epithelial cells but the characteristics of each response differs. Activation of calcium-dependent chloride secretion was thought, until recently, to be stimulated primarily through opening of $Ca^{2+}$-activated $K^+$ channels which by increasing the negative intracellular potential increases the driving force for apical membrane chloride secretion. Recently, the presence of a distinct $Ca^{2+}$-dependent chloride channel (CaCC) in the apical membrane of polarized T84 cells was described, although the molecular identity of the channel remains undefined.

It was first noted in the late 1980's that calcium-dependent responses in intestinal epithelial cells were short-lived unlike most cyclic nucleotide-dependent responses. Barrett hypothesized that additional inhibitory second messengers antagonize the effects of calcium within the epithelial cell and that this accounts for the termination of the calcium-dependent chloride secretory response. Her laboratory and that of Traynor-Kaplan have been at the forefront of investigations to define the 'negative pathways' stimulated by carbachol, a prototypic calcium-dependent chloride secretagogue and have identified intracellular messengers which appear to negatively influence calcium-mediated chloride secretion. These include: influx of extracellular calcium, generation of inositol (3,4,5,6)-tetrakisphosphate ($IP_4$), activation of protein kinase C, and a tyrosine kinase-dependent signaling pathway.

Thus the major clinical phenotype of cystic fibrosis results from an absence of normal cAMP-regulated chloride transport.

Despite this knowledge, no one has been able to use this information to develop a truly effective treatment for CF. Current treatments are aimed to prevent or treat the pulmonary infections and the adverse physiological consequences of those infections. But no treatment reverses the cystic fibrosis defect in ion transport which, in turn, would lead to normal levels of water within the lumen of the lungs. Preventing the desiccation of the lungs by overcoming the defective ion transport would allow patients with cystic fibrosis to avoid pulmonary infections. Thus, there is a great need for a therapy to overcome or alleviate the defect in ion transport.

By treatment is meant at least an amelioration of the symptoms associated with the mucin secretion associated pathological condition afflicting the host, where amelioration is used in a broad sense to refer to at least a reduction in the magnitude of a parameter, e.g. symptom, associated with the pathological condition being treated, such as excess mucus, insufficient mucus, etc. As such, treatment also includes situations where the pathological condition, or at least symptoms associated therewith, is completely inhibited, e.g. prevented from happening, or stopped, e.g. terminated, such that the host no longer suffers from the pathological condition, or at least the symptoms that characterize the pathological condition.

The present compounds may be used to treat subjects including animals, and in particular, mammals, including humans, as patients. Thus, humans and other animals, and in particular, mammals, suffering from diseases or disorders related to CaCC, can be treated, ameliorated or prevented by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents (depending upon the disease to be treated).

Treatment according to the present invention can also be administered in conjunction with other conventional therapies, e.g., treatment in conjuction with other therapeutics used to treat CaCC related disorders and/or other therapeutics used to treat cystic fibrosis.

IV. Mechanism and Optimization

One goal was to find a number of compounds that would increase intracellular $Ca^{2+}$ using the ECaT Ringer's solution (FIG. 8) which was shown to be essential for obtaining a sustained $Ca^{2+}$ signal induced by Zinc. Zinc, used in the screening as a positive control, produced a long lasting increase in cytoplasmic $Ca^{2+}$ by targeting the P2X purinergic receptor in the ECaT Ringer's. $Na^+$ is 100 times more abundant than $Ca^{2+}$ in the normal Ringer's solution, and $Na^+$ transfer will predominate over $Ca^{2+}$ for entry when the P2X receptor non-selective cation channels open. Thus for the ECaT Ringers, we eliminated $Na^+$ from the solution and replaced it completely by N-methyl-D-glucamine (NMDG) to maintain the solution osmolality to favor $Ca^{2+}$ for entry through the P2X receptor. We were searching for compounds that activate the P2X receptor channel or other $Ca^{2+}$ entry channels, as well as compounds that bind to membrane or cellular proteins which are involved in intracellular $Ca^{2+}$ regulation.

Compounds were selected as potential hits if their change of fluorescence ratio fell within 3 SD of those obtained for zinc (ratio), and larger than that recorded for DMSO (ratio) +3SD. The average Z factor of all 25 plates is 0.6 for the 15 min detection. Hits were solely based on the change in the fluorescence ratio. Any compound that was highly auto-fluorescent was not considered further.

Figures 10, 11A:
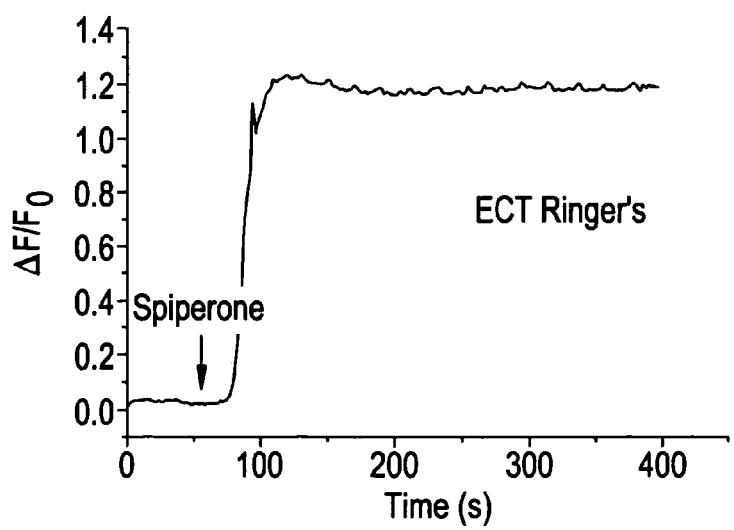
FIG. 10 shows various compounds from the high throughput screening with $EC_{50}$<50 μM in stimulating the increase of intracellular calcium.

The screening yielded 67 compounds that met the screening criteria and were selected as potential hits. Among those potential hits, 28 compounds are not commercially available. 2 compounds are known to create pores in the membrane. Based on these criteria, those 30 compounds were eliminated from further study. We further evaluated 37 hits manually using the Fluorescence Plate Reader system. FIG. 10A illustrates the change in fluorescence ratio for three of the hits compared to zinc and 5% DMSO. During the evaluations, 18 compounds induced an increase $Ca^{2+}$ that never did reach to a maximum plateau value and were also not studied further. Following this initial vetting process, the half-maximal effective concentration ($EC_{50}$) was determined of each of the remaining 19 molecules. Eight of those compounds had an $EC_{50}$ of less than 50 µM (FIG. 10). A sample of the $EC_{50}$ curve of three compounds plus zinc is shown in FIG. 10B. Spiperone showed the best $EC_{50}$. In addition, Spiperone has a dual effect on the intracellular $Ca^{2+}$, an activation and inhibition. Spiperone stimulates cytoplasmic $Ca^{2+}$ at lower concentrations (<50 µM), but the stimulation is reduced at higher spiperone concentrations (>50 µM).

Figure 11B:
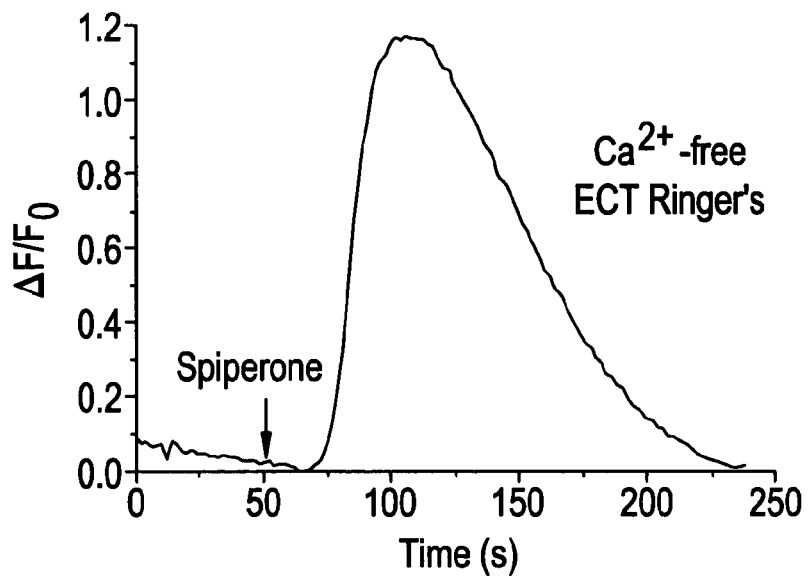
FIG. 11 shows spiperone-stimulated calcium increase under varying saline solutions in IB3-1 cells.
Figure 11C:
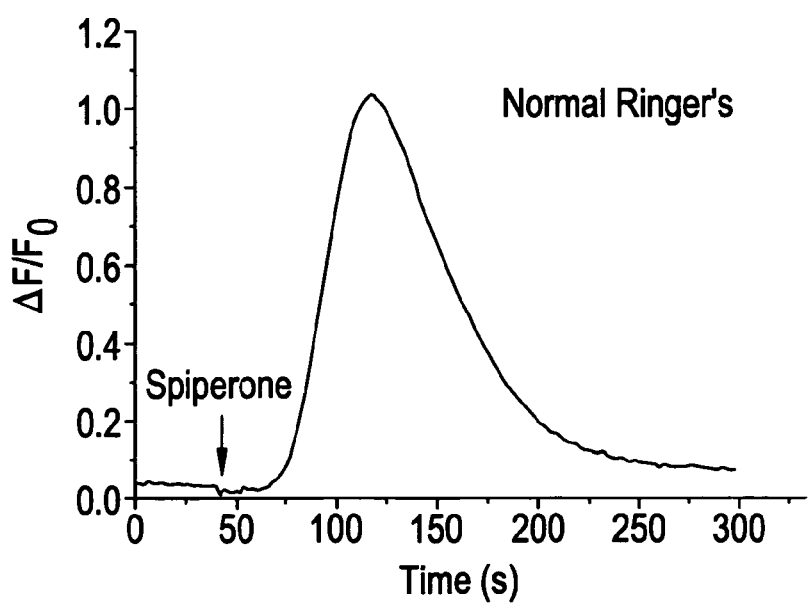
Figure 11D:
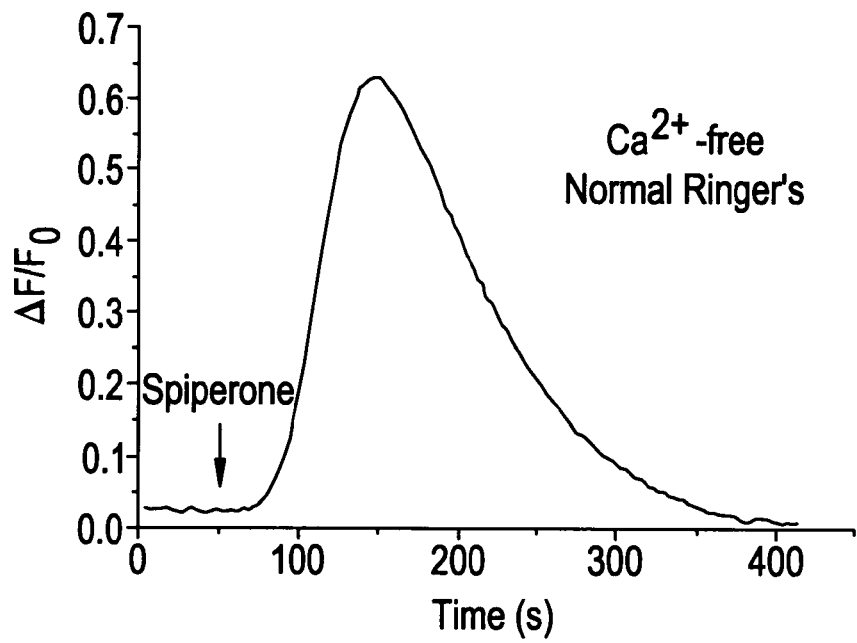

Because spiperone was the most potent of the intracellular $Ca^{2+}$ enhancers ($EC_{50}$=9.3), its mechanism of action was further investigated. A microscope-based fluorescence $Ca^{2+}$ measurement system was utilized in this study. First IB3-1 cells grown on a coverglass were bathed in the ECaT Ringer's which was used for the screen. The challenge with spiperone produced a sustained increase in $Ca^{2+}$ (FIG. 11A). In order to ascertain the origin of this sustained increase the experiment was repeated except with $Ca^{2+}$-free ECaT Ringer's solution, (See FIG. 8). In the absence of extracellular $Ca^{2+}$, the cells showed only a transient increase in cytoplasmic $Ca^{2+}$ (FIG. 11B).

Figure 12A:
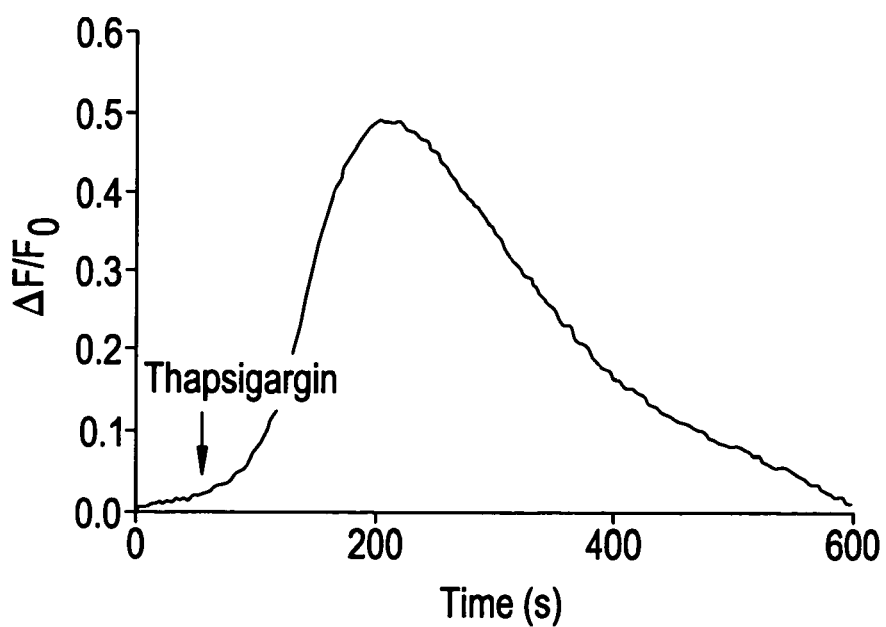
FIG. 12 Spiperone released $Ca^{2+}$ from the endoplasmic reticulum (ER) through a PLC- and protein tyrosine kinase-dependent pathway in IB3-1 cells.
Figure 12B:
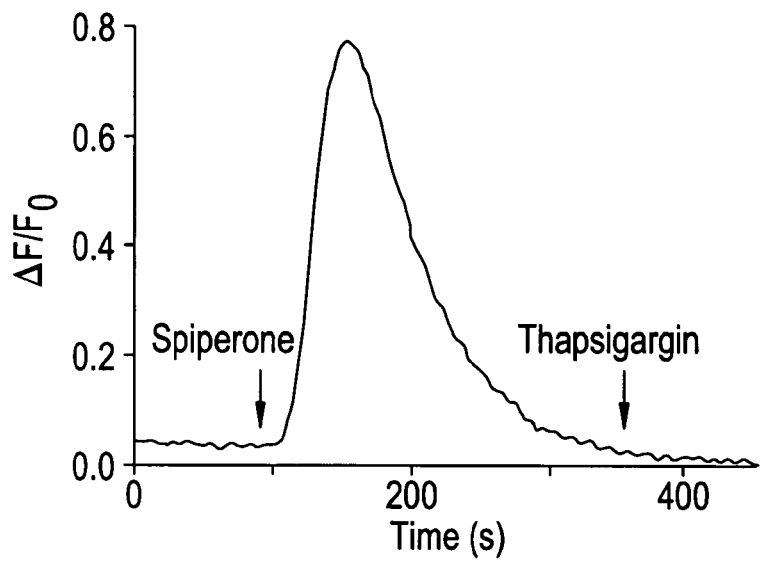
Figure 12C:
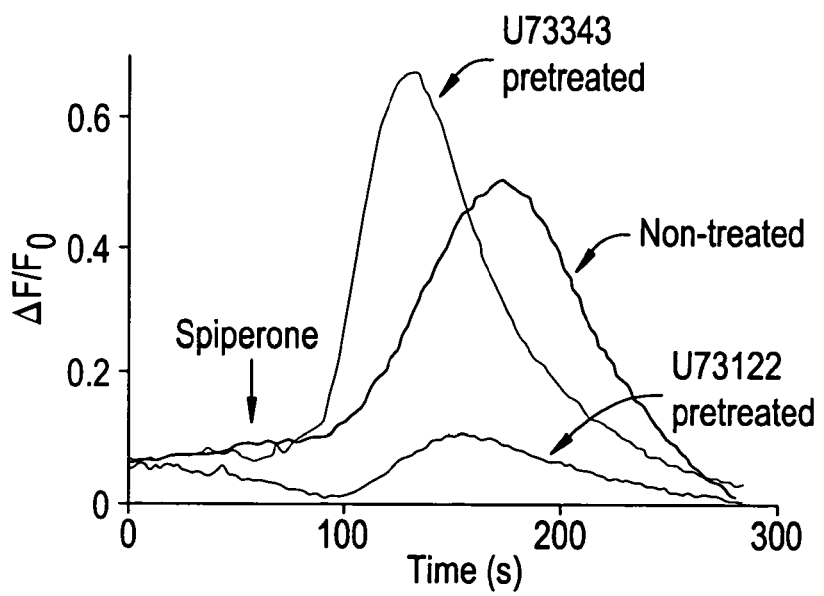
Figure 12D:
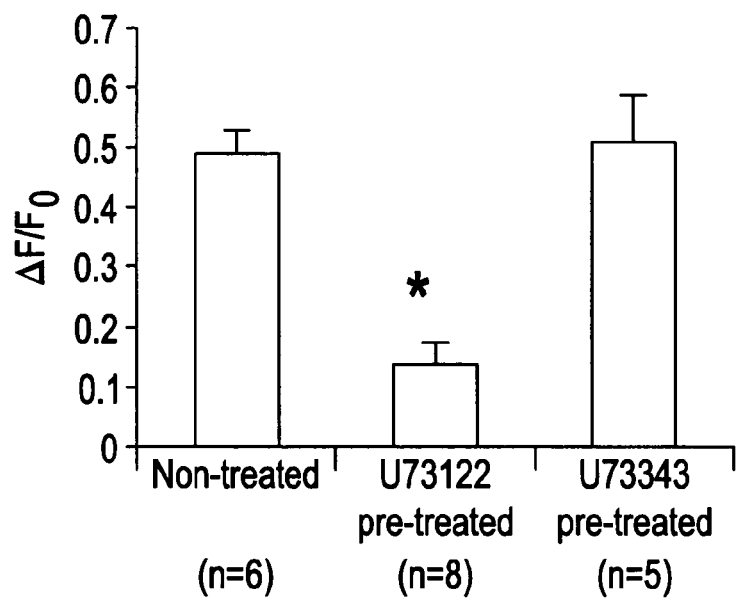

Also tested was spiperone's effect on $Ca^{2+}$ change in cells bathed in normal Ringer's (which contains the usual levels of $Ca^{2+}$, $Na^+$ and $Mg^{2+}$) and in $Ca^{2+}$-free normal Ringer's solution (FIG. 8). As shown in FIGS. 12C and 12D, spiperone again induced only a transient increase in $Ca^{2+}$ in both solutions.

The results above indicate that spiperone stimulates a sustained increase in cytoplasmic $Ca^{2+}$ in the ECaT Ringer's. Spiperone's induction of only a transient increase in cytosolic $Ca^{2+}$ under normal and $Ca^{2+}$-free normal Ringer's solutions points to intracellular stores as the source for the transient increase.

Using normal Ringers, a study was undertaken to determine whether the source of the increase in cytoplasmic $Ca^{2+}$ was indeed the endoplasmic reticulum (ER). As part of the normal $Ca^{2+}$ transit system across the ER, the $Ca^{2+}$-ATPase pumps $Ca^{2+}$ from the cytosol to the ER uphill against the concentration gradient. Other channels continue to cycle $Ca^{2+}$ from ER back to cytosol. Thapsigargin blocks the $Ca^{2+}$-ATPase, inhibiting the uphill uptake. IB3-1 cells were treated with thapsigargin, producing a net increase in $Ca^{2+}$ in the cytosol originating from the ER (FIG. 12A). When the cells were treated with spiperone before their dose of thapsigargin, there was no increase in cytosolic $Ca^{2+}$ after the thapsigargin treatment (FIG. 12B). The difference in these reactions to thapsigargin suggests that spiperone had emptied the ER of $Ca^{2+}$.

Phospholipase C (PLC) is an intracellular enzyme that participates in calcium signaling pathways. To establish whether spiperone acts through PLC-dependent pathways to increase cytosolic $Ca^2$ the IB3-1 cells were preincubated with U73122, a known PLC-inhibitor, and U73433, a chemical analog of U73122 that does not inhibit PLC. The pretreatment by U73122 diminished the spiperone-induced $Ca^{2+}$ transient, but pretreatment by U73433 did not. Results are shown in FIG. 12C and summarized in FIG. 12D. These data suggest that when PLC is inhibited, spiperone cannot enhance cytosolic $Ca^{2+}$, which in turn suggests that spiperone releases ER $Ca^{2+}$ through a PLC-dependent pathway. 2APB is an inhibitor of the $IP_3$ receptor on the ER membrane. $IP_3$ is the downstream molecule of PLC. 30 minutes incubation with 2APB (100 µM) totally blocked the spiperone induced $Ca^{2+}$ release from ER (data not shown), which also suggests the PLC pathway is involved in the spiperone-stimulated $Ca^{2+}$ release mechanism.

Figure 12E:
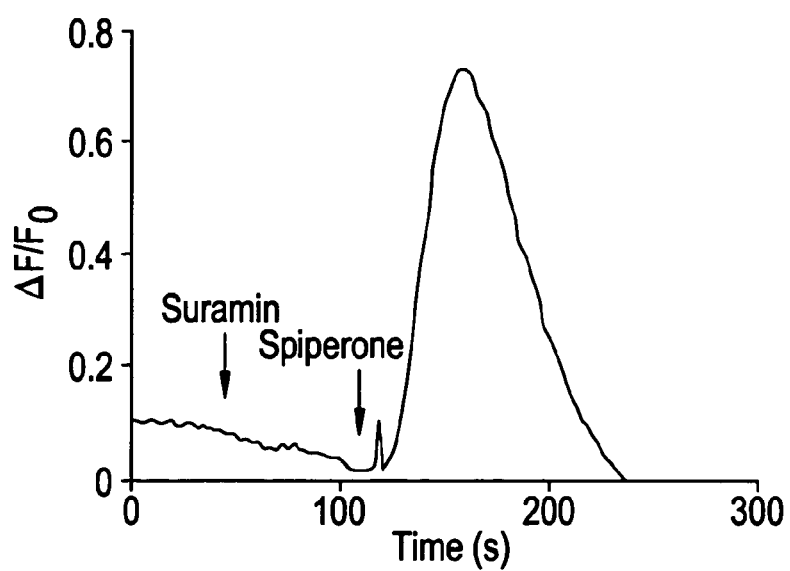
Figure 12F:
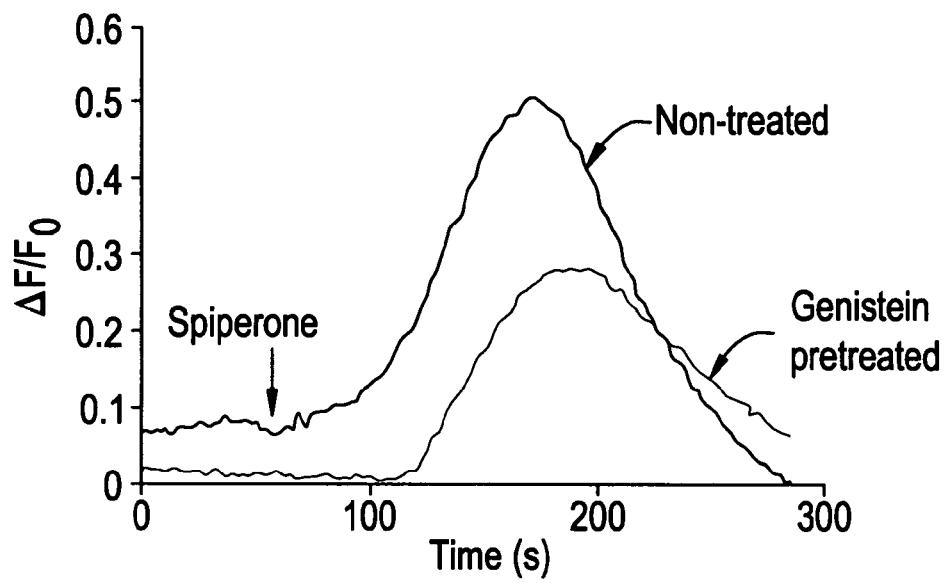
Figure 12G:
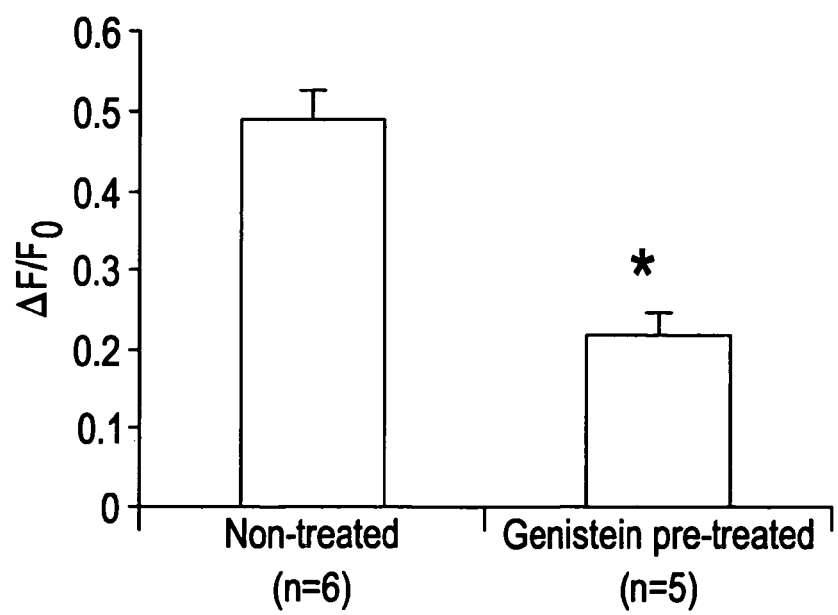

There are two major molecules that activate PLC pathways to release $Ca^{2+}$ from the ER. One is the G-protein coupled receptors. The second is the protein tyrosine kinase (PYK). To establish which pathway was affected by spiperone, one set of IB3-1 cells was incubated with suramin, a general G protein-coupled receptor antagonist, and incubated another set with genistein, a non-selective PYK inhibitor. Suramin did not reduce the spiperone-stimulated increase in $Ca^{2+}$, but genistein partially blocked the increase (FIGS. 12E and 12F). (FIG. 12G is the summary data of genistein treatment.) Lavendustin A is another protein tyrosine kinase inhibitor. Addition of lavendustin A (10 µM) significantly diminished the increase in $Ca^{2+}$ induced by spiperone in IB3-1 cells (data not shown). All the data suggest that spiperone enhances the ER's release of $Ca^{2+}$ by targeting a PYK-coupled PLC pathway.

Figure 13A:
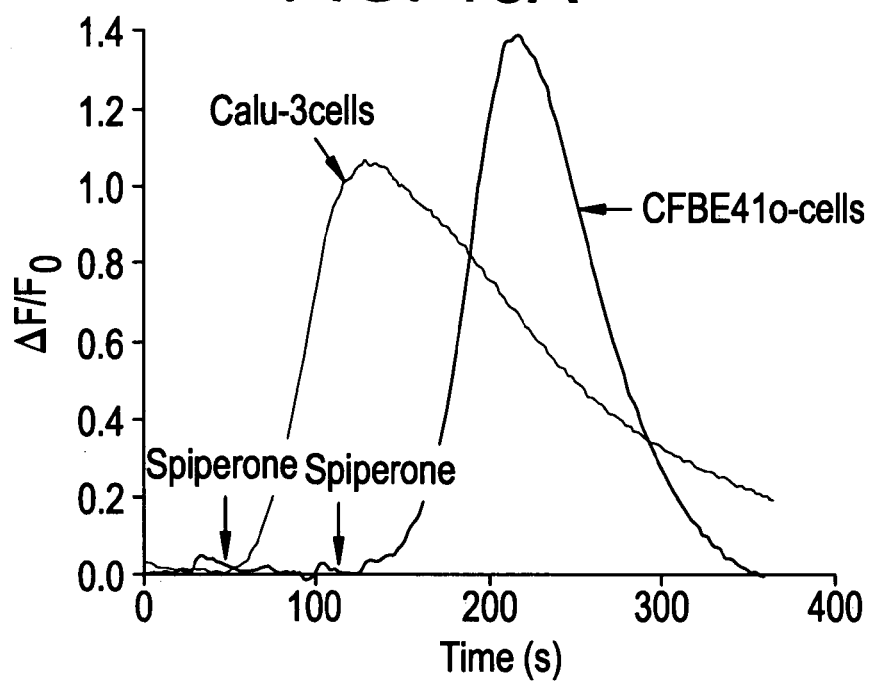
FIG. 13 Spiperone also stimulated a transient release of $Ca^{2+}$ in Calu-3 (non-CF) and CFBE41o-(CF) human airway epithelial cells and in primary cultures of normal human epithelial cells (NHBE).
Figure 13B:
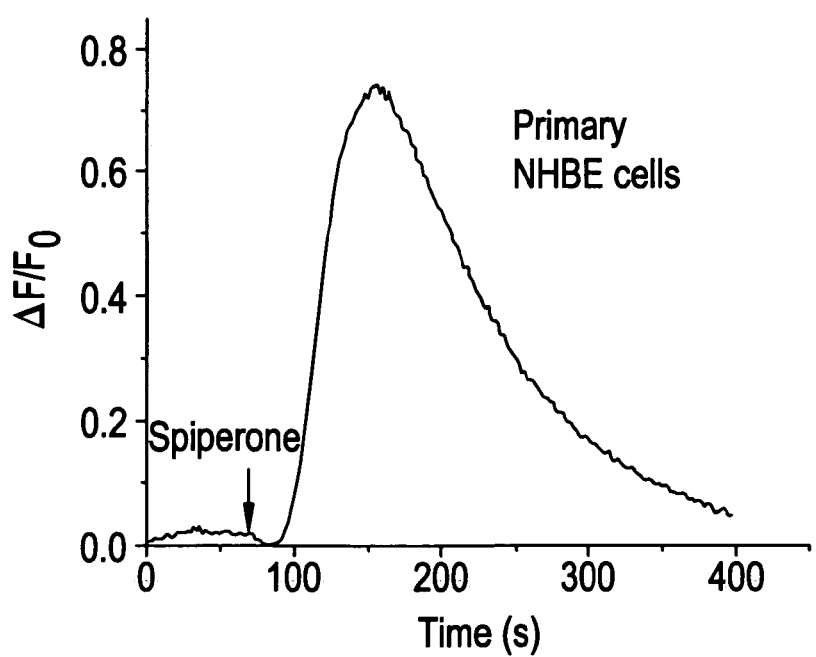

To assess whether spiperone induces the release of $Ca^{2+}$ from other cell types, its effect on Calu-3 cells, a non-CF human sub-mucosal gland serous epithelial cell line, CFBE41o-cells, a CF human bronchial epithelial cell line which contains homozygous ΔF508-CFTR mutations, and NHBE, a primary normal human bronchial/tracheal epithelial cells, was tested. As in the IB3-1 cells, spiperone induced a transient increase in $Ca^{2+}$ in Calu-3 non-CF, CFBE41o-CF and NHBE primary culture cells (FIG. 13).

An experiment was carried out to establish that the spiperone-induced increase of $Ca^{2+}$ would produce an increase in $Cl^-$ transport relevant to CF, and that it would do so in CF relevant epithelial cells. Calu-3 and CFBE41o-cell monolayers were cultured on permeable filter support and "short circuit current" measurements were performed to evaluate the current produced by Cl⁻ in these cells.

Na⁺ is a positively charged ion and its absorption would interfere with the short circuit measurement for Cl⁻ secretion. Therefore, in normal Ringer's solution, Na⁺ absorption across the cell membrane was blocked with amiloride. Cell monolayers were then exposed to the two relevant compounds: niflumic acid (NFA), which is a non-selective CaCCs blocker or to CFTR$_{inh}$-172, which is a specific CFTR blocker.

Figure 14A:
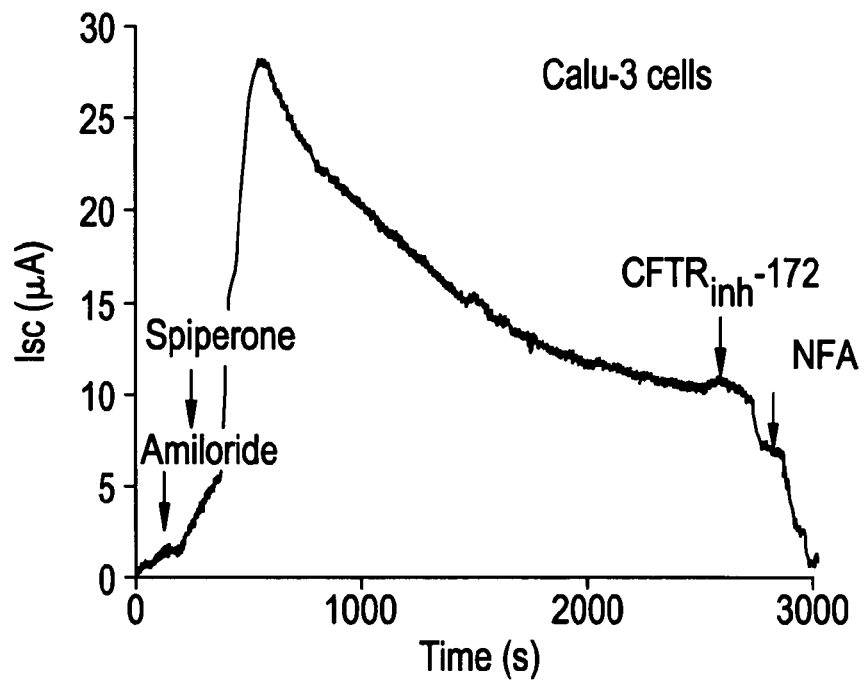
FIG. 14 Spiperone (20 μM) stimulated $Cl^-$ secretion in Calu-3 (A-B) and CFBE41o-(C) human airway epithelial cells in monolayers.
Figure 14B:
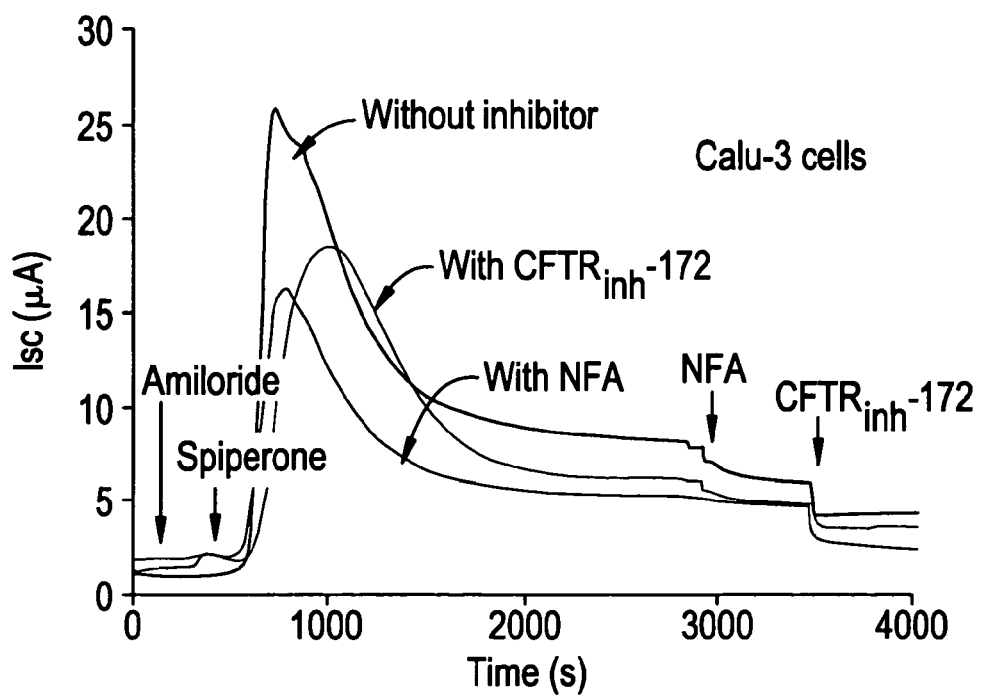

In Calu-3 cells, the non-CF line, spiperone produced a transient and then a sustained Cl⁻ current. FIGS. 14A and B show how transient Cl⁻ was reduced by NFA and CFTR$_{inh}$-172, and the sustained Cl⁻ release was totally blocked. These results indicate that, at least in Calu-3 cells, spiperone not only activates the CaCCs but also may activate other Cl⁻ channels including CFTR.

Figure 14C:
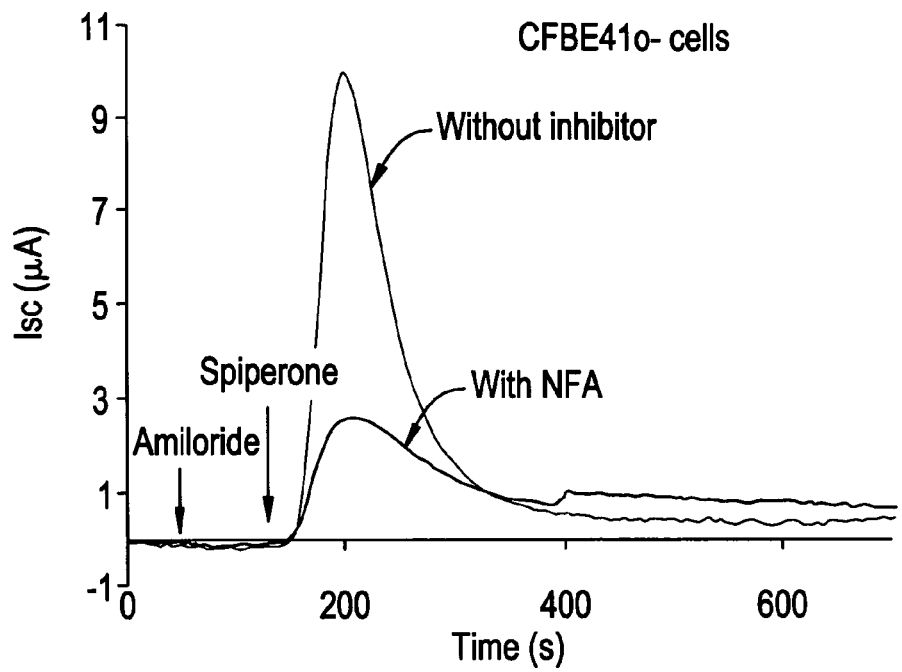
Figure 14D:
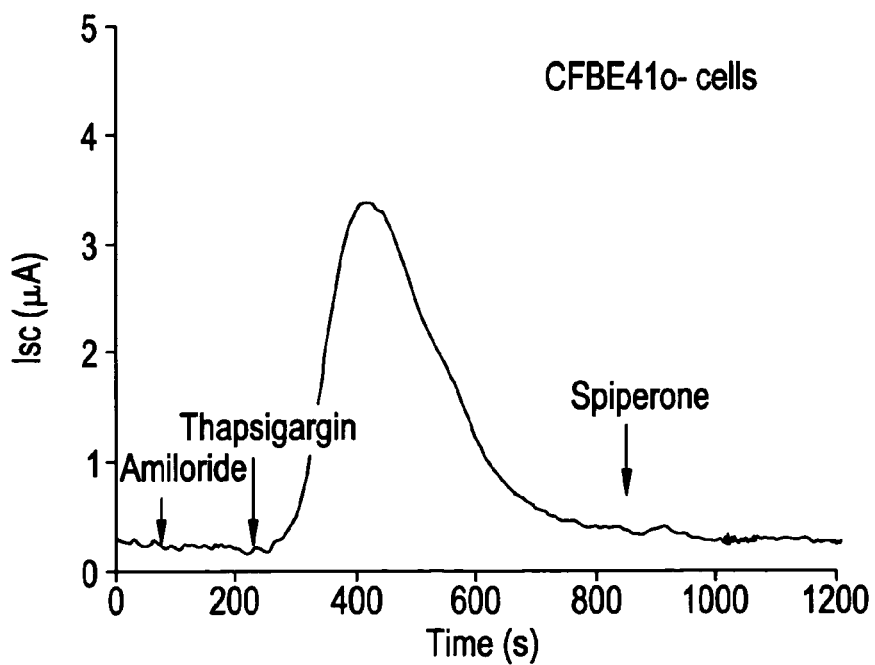

In CFBE41o-cells, the CF cell line, spiperone caused only a transient Cl⁻ secretion. When the CaCCs were blocked by NFA, spiperone's effect on Cl⁻ secretion was reduced significantly (FIG. 14C). We further evaluated CaCC function in CFBE41o-cells by adding thapsigargin to the cells. As shown in FIG. 14D, thapsigargin blocked the uptake of Ca²⁺ back into the ER, causing a transient increase in Cl⁻ secretion. Subsequent application of spiperone failed to stimulate any additional Cl⁻ transit. Taken together our data suggest that spiperone's effect on CFBE41o-cells is to increase intracellular Ca²⁺ from the ER, which in turn activates CaCCs and produced a transient increase in Cl⁻ secretion.

Figure 15A:
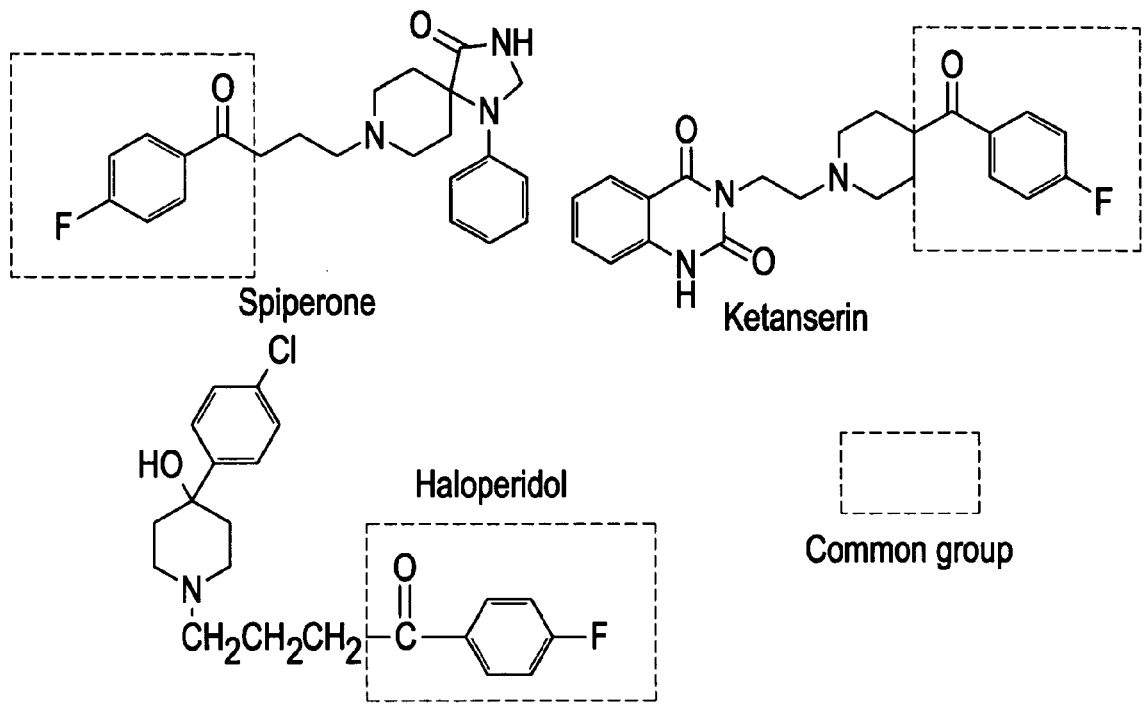
FIG. 15 Ketanserin and haloperidol did not release $Ca^{2+}$ or increase $Cl^-$ secretion in human airway epithelial cells.

To assess whether spiperone's antipsychotic effects were related to its function as an enhancer of Ca²⁺ transit and Cl⁻ secretion, spiperone analogs haloperidol and ketanserin were evaluated. Spiperone and haloperidol have a high affinity for and are antagonists to the dopamine D₂ receptor. Spiperone and ketanserin have a high affinity for and are antagonists to 5-HT₂ (5-hydroxytryptamine) receptor. In addition, as shown in FIG. 15A, the structure of all three drugs includes the 1-carbonyl oxygen atom and 4-flurobenzoyl moiety.

Figure 15B:
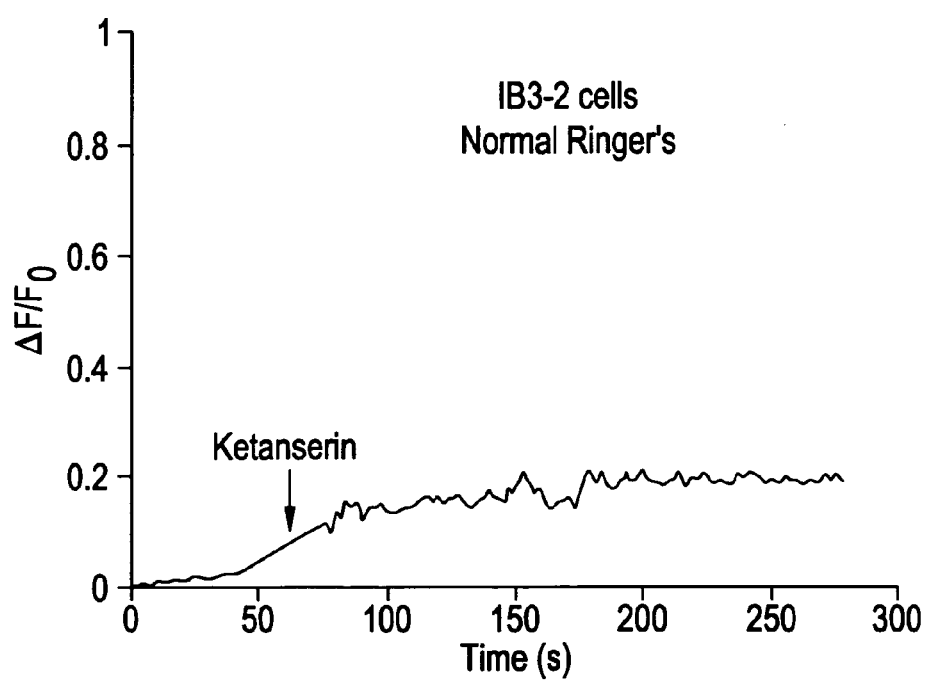
Figure 15C:
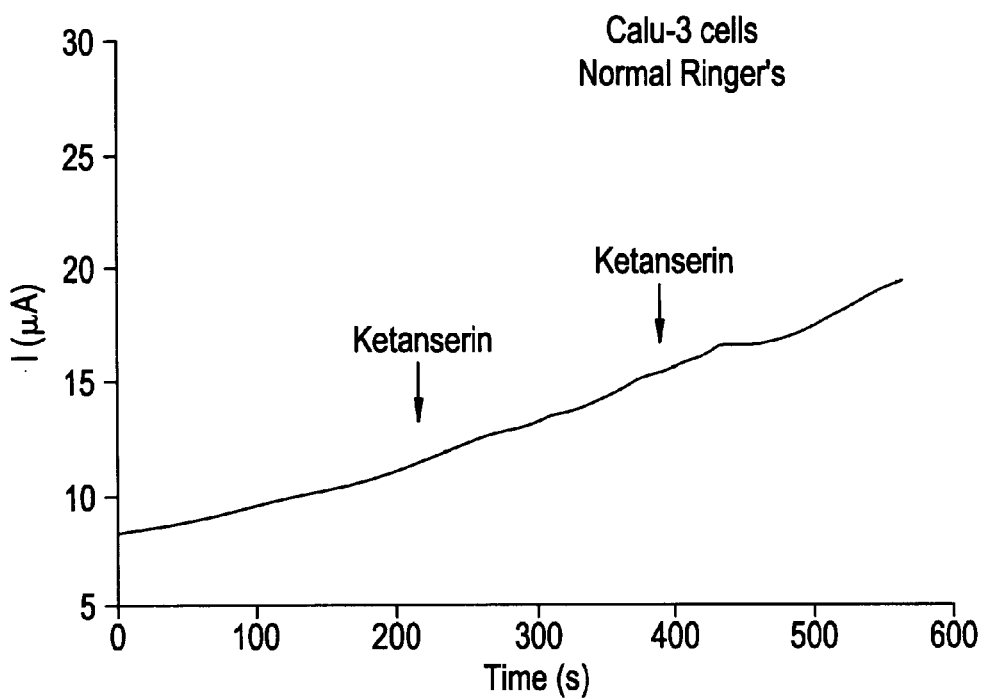
Figure 15D:
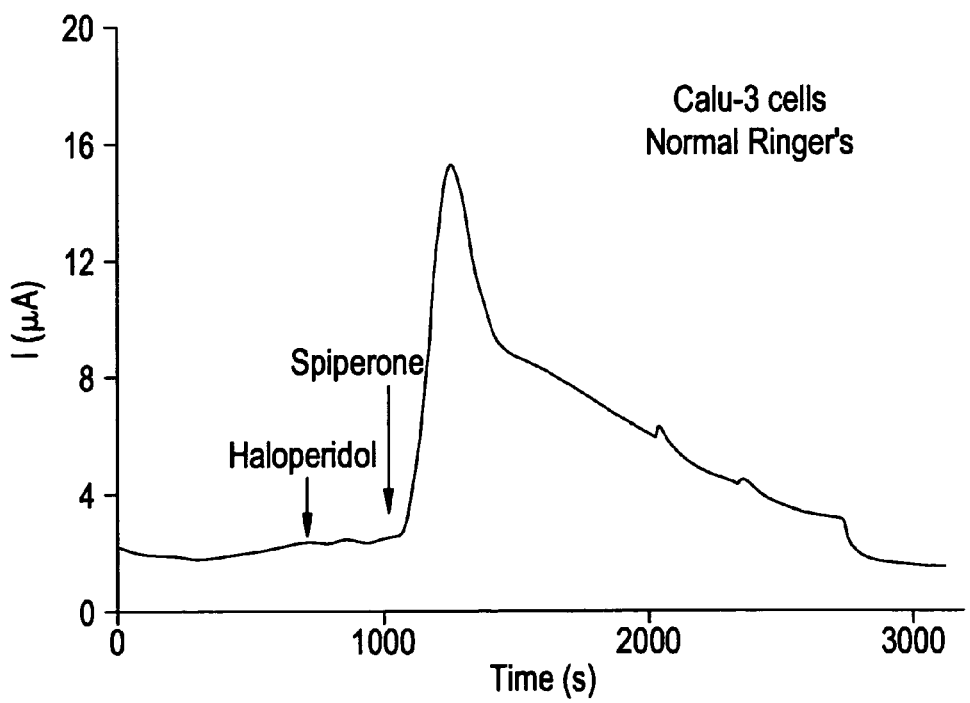
Figure 15E:
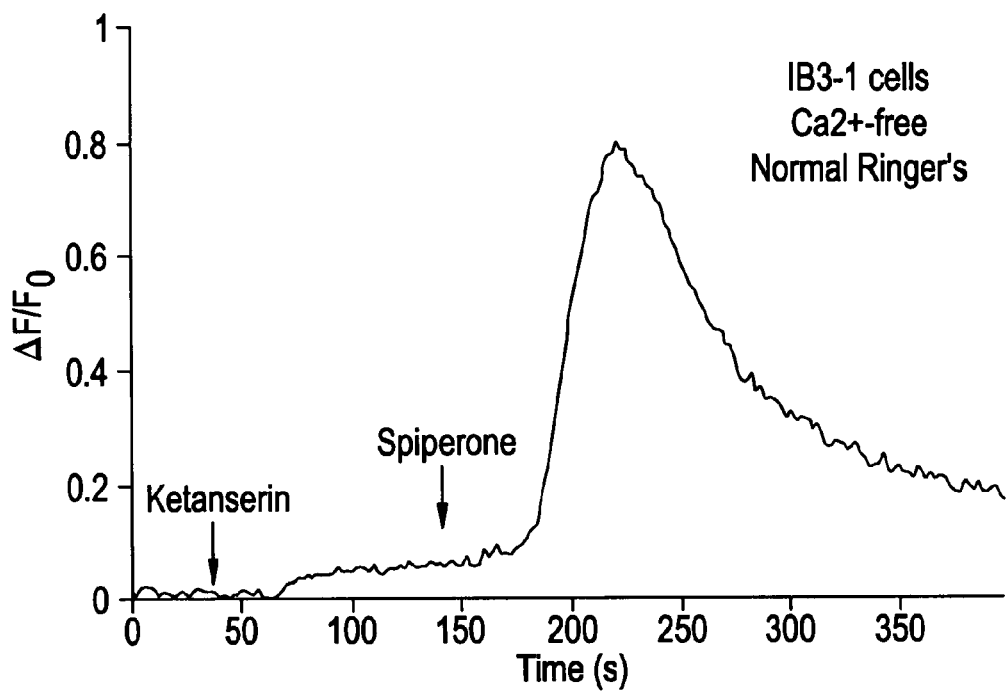
Figure 15F:
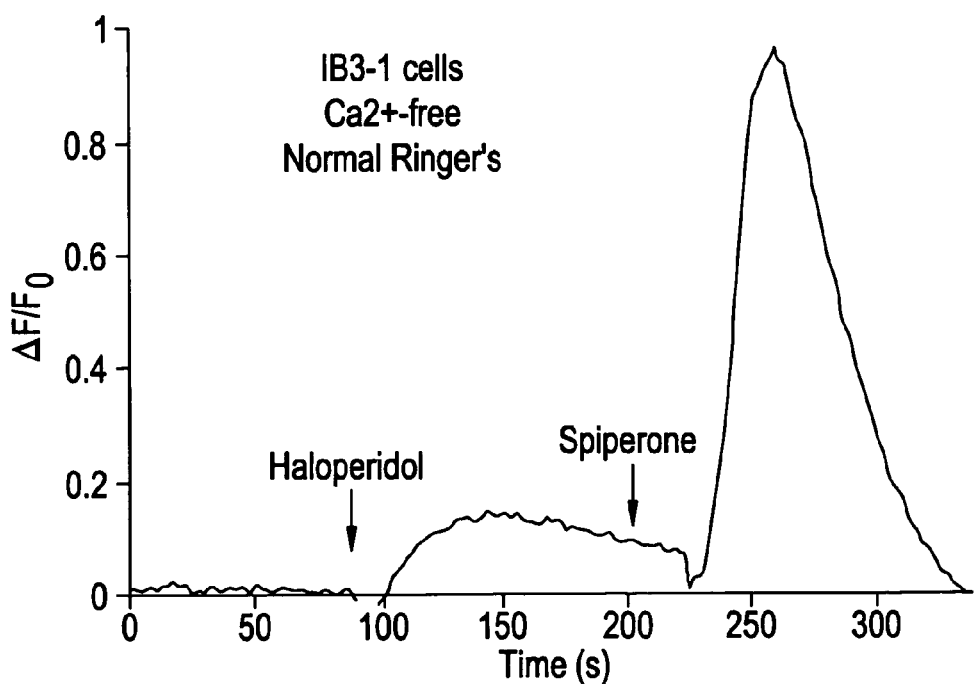

It was found that ketanserin did not increase intracellular Ca²⁺ in IB-3 cells, nor Cl⁻ secretion in Calu-3 cells (FIGS. 15B and 15C). Haloperidol did not stimulate the Cl⁻ current in Calu-3 cells and did not prevent spiperone from stimulating transepithelial Cl⁻ currents (FIG. 15D). Both ketanserin and haloperidol were added to the IB3-1 cells prior to adding spiperone, and spiperone was still able to stimulate a transient increase in Ca²⁺ in the Ca²⁺-free normal Ringer's solution (FIGS. 15E and 15F respectively).

These data suggest that although ketanserin, haloperidol and spiperone belong to the same antipsychotic drug family, their ability to induce an increase in Ca²⁺ and Cl⁻ secretion in human airway epithelial cells is completely different. The data also indicate that spiperone has a different function in airway cells outside of its known behavior as an antagonist of 5-HT₂ and dopamine D₂ receptors.

Figure 16A:
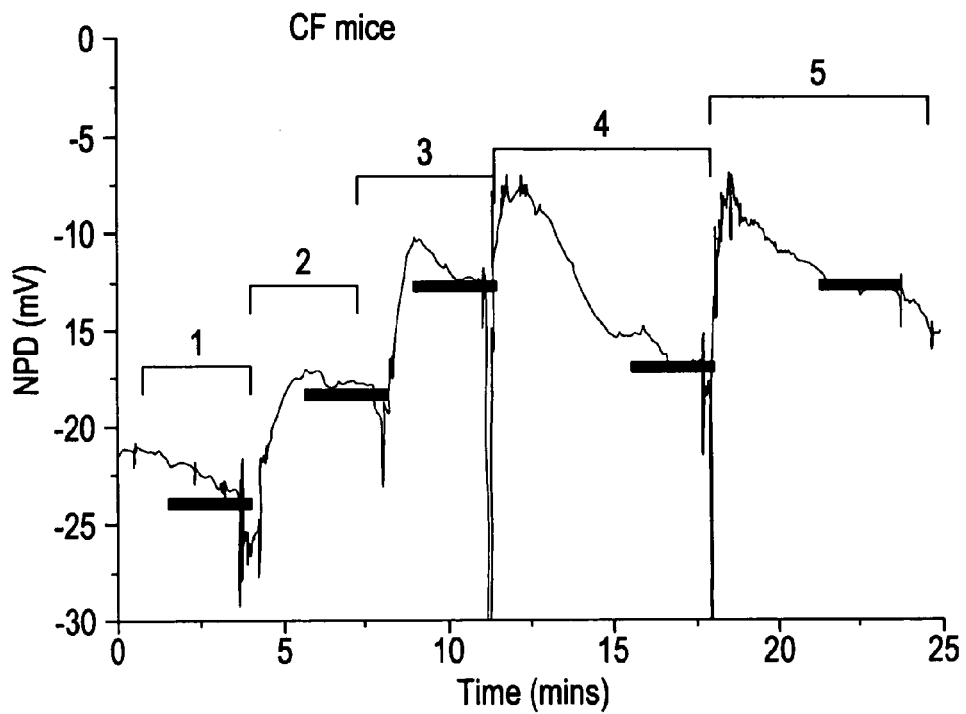
FIG. 16 Spiperone increased the $Cl^-$ conductance of the nasal epithelium of CFKO mice, but not wild-type mice.
Figure 16B:
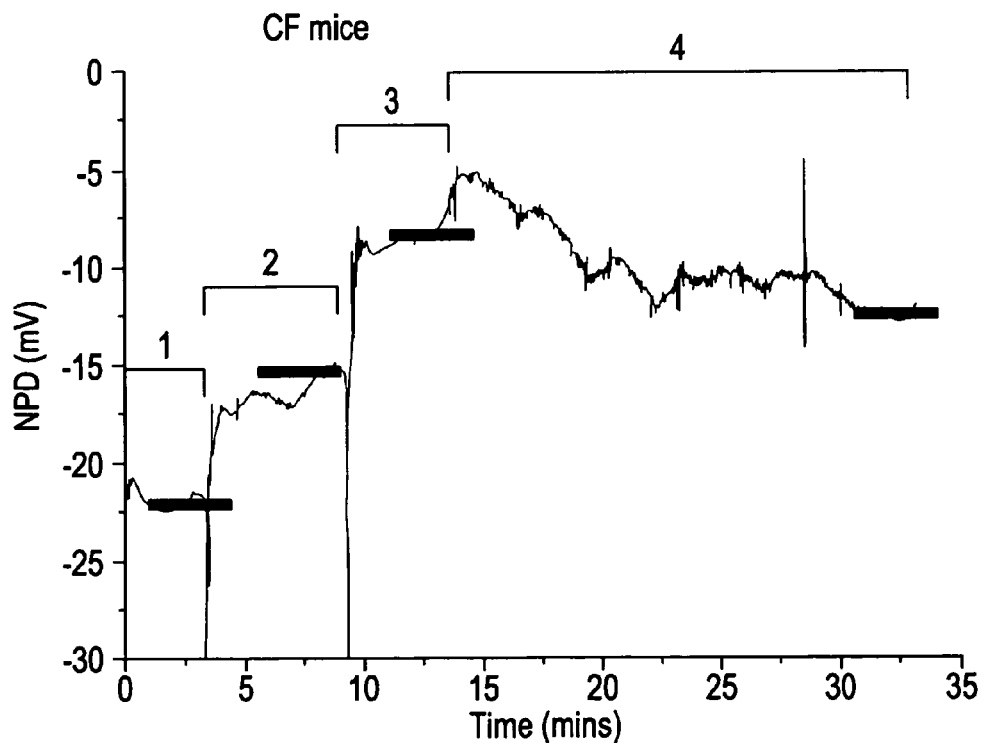
Figure 16C:
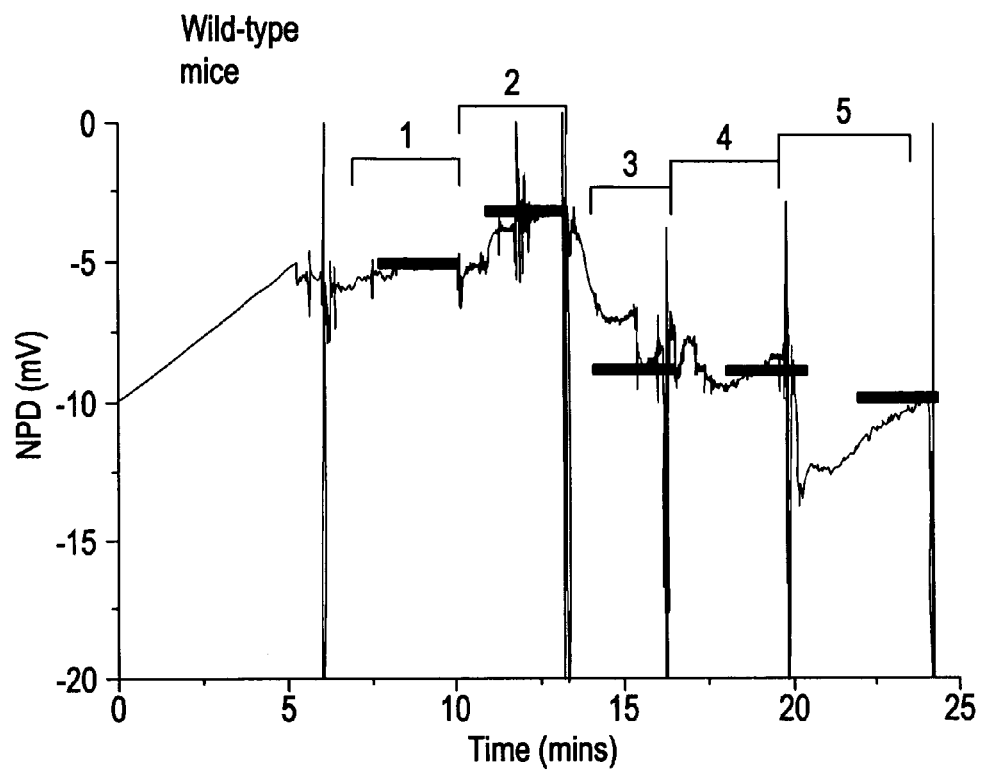
Figure 16D:
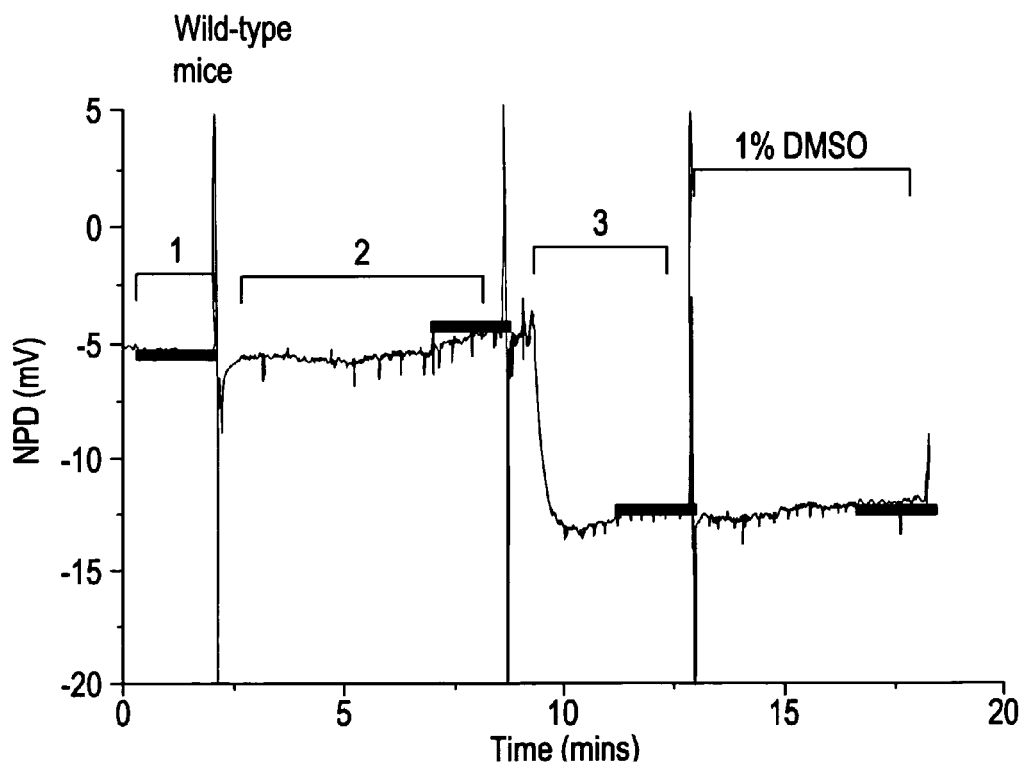
Figure 16E:
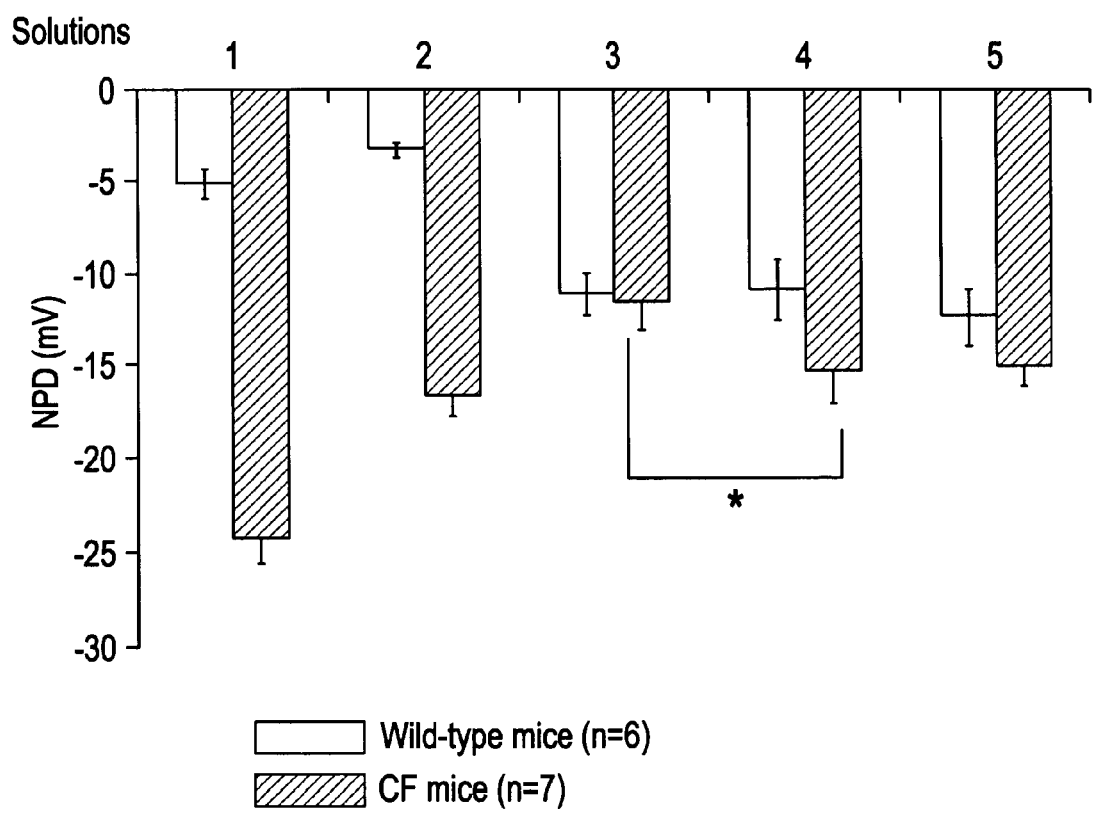

To assess the hypothesis that spiperone will stimulate chloride secretion in vivo, the nasal potential difference in CF (double transgenic CFKO) and wild-type (C57Bl/6) mice were tested. FIGS. 16A and B show results from CF mice and FIGS. 16C and D show wild-type mice. FIG. 16E shows the average NPD value from the CF mice and wild-type mice. As spiperone was topically applied to the nasal epithelia of the mice, sodium and chloride transport were assessed by measuring the voltage difference between the electrodes.

As expected for CF mice that hyperabsorption of Na⁺ and have no CTFR, the nasal potential difference (NPD) was significantly hyperpolarized when the nares were perfused with baseline Ringer's solution (FIG. 8). In order to allow for later hyperpolarization from chloride secretion, their nasal epithelia were perfused with baseline Ringers with amiloride added to block the epithelial Na⁺ channel. For the next perfusion, the Cl⁻ was removed by substituting Na⁺ gluconate in the baseline Ringer's solution (FIG. 8), then removed Cl⁻ from the mucosa by perfusing the nare with that Ringer's. This rinse further depolarized the epithelia, since these mice have no functioning CFTR.

The mouse nasal epithelia was perfused with the Zero Cl⁻ baseline Ringer's with spiperone (1 µM), which hyperpolarized the mouse nasal potential significantly, and indicated that the spiperone induced an increase in Cl⁻ conductance. Subsequent increases in the concentration of spiperone (20 µM) did not boost Cl⁻ conductance (FIG. 16A and summarized in FIG. 16E). After 19 min of sustained perfusion, the NPD of the CF mouse remained significantly hyperpolarized by spiperone at 1 µM, indicating that spiperone continuously stimulated nasal Cl⁻ secretion in the CF mouse (FIG. 16B).

In wild-type C57Bl/6 mice, after we eliminated their mucosal Cl⁻, CFTR chloride channel was activated in the airway cells, secreted Cl⁻, and hyperpolarized the NPD. It was striking that adding spiperone did not induce any further hyperpolarization, which indicates that spiperone is unable to stimulate additional Cl⁻ conductance in nasal epithelia with normally functioning CFTR (FIG. 16C and the summary data is in FIG. 16E). The 1% DMSO control did not stimulate Cl⁻ secretion in the wild-type mice (FIG. 16D).

By using a screening assay, a large number of compounds in the MSSP 2000 spectrum library were rapidly accessible to identify spiperone as a most potent Ca²⁺ enhancer. The discovery of spiperone also indicates a potential new CF therapy platform.

Several therapies that stimulate Cl⁻ via increases in intracellular Ca²⁺ are currently under development. ATP and UTP operating through a P2Y2 purinergic receptor were proposed in the early 1990s to rescue Cl⁻ secretion through the activation of CaCCs. Because these nucleotides are easily hydrolyzed by exonucleotidases, a non-hydrolyzed form of UTP INS 37217 (denufosol) was developed. A primary endpoint for the phase III clinical trial of inhaled denufosol tetrasodium was recently completed. A 2.5% improvement in lung function was reported over 24 weeks of treatment. Moli1901 interacts with the phospholipids in the membrane and activates CaCC by elevating the intracellular calcium concentration. It stimulated Cl⁻ secretion through CaCC in normal and CF airway epithelia. The inhalation of nebulized Moli1901 was well tolerated in the CF patients in a phase II clinical trial. Moli1901 showed a sustained effect in improving lung function.

Spiperone works via a PLC signaling pathway, because phospholipase C (PLC) inhibitor U73122 partially inhibited the spiperone-induced Ca²⁺ increase. PLC is an enzyme with a family of 13 isoforms divided into 6 different subfamilies: PLC-β, PLC-γ, PLC-δ, PLC-ε, PLC-ζ, and PLC-η. The PLC-β family is typically considered to be activated by a G-protein coupled receptor, while the PLC-γ family is activated by protein tyrosine kinase receptors (PYKs).

In general, tyrosine kinase receptors regulate human airway goblet cell mucin secretion through a PLC-dependent pathway. Two major cell surface receptor tyrosine kinases, the epidermal growth factor receptor and the platelet-derived growth factor receptor families are both the potential therapeutic targets in pulmonary diseases due to their important roles in chronic tissue remodeling in asthma, bronchitis and pulmonary fibrosis. The spiperone-induced increase in Ca²⁺ was blocked by genistein and lavendustin A, two general tyrosine kinase inhibitors. This result suggests that spiperone affects a protein tyrosine kinase, activating the PLC pathway to release $Ca^{2+}$ from the ER.

Spiperone acts in a similar way in several human airway epithelial cells including CF cell lines IB3-1 and CFBE41o-, non-CF cell line Calu-3 which highly expresses CFTR, as well as one primary cell culture, NHBE. Importantly in all four cell types in $Ca^{2+}$-free Ringers, spiperone stimulated transient increases in cytosolic $Ca^{2+}$.

The important question now became whether this increase in cytoplasmic $Ca^{2+}$ would translate into $Cl^-$ secretion that would be of potential benefit in CF. The results indicate that spiperone activates CaCCs in both CFBE41o- and Calu-3 cells and induces them to secrete $Cl^-$. In a more surprising result, in Calu-3 cells, spiperone is involved in CFTR activation as well.

Looking at $Cl^-$ channels in vivo, it is noted that CaCC is down-regulated in cells containing normal CFTR and up-regulated in CF cells where CFTR is compromised. For example, in intact murine CF tracheal epithelia, application of UTP leads to a robust increase in $Cl^-$ secretion through CaCC.

The results with spiperone in the wild-type and CF knock-out mice follow this pattern exactly. In normal mice, the CaCC is down regulated, and in the CF mice, it is upregulated. In our experiments in CF mice, spiperone stimulated a significant and sustained increase in nasal potential difference that indicated enhanced $Cl^-$ secretion in the CF mouse. By contrast, in normal mice the nasal potential difference did not change following exposure to spiperone. The observation that spiperone stimulates $Cl^-$ secretion, both in human CF cell lines and in intact nasal epithelium from CFTR knockout mice enhances spiperone's potential therapeutic value.

Since spiperone is an antipsychotic, an investigation was carried out to determine whether its antipsychotic mechanism could be tied to its ability to stimulate $Cl^-$ secretion. To find out, spiperone was compared with two of its analogs, haloperidol and ketanserin. Spiperone has a high affinity for, and is an antagonist of, dopamine $D_2$ receptors with an IC50 of 10 nM. Dopamine itself, on the other hand, is the ligand of the dopamine $D_2$ receptor and stimulates $Na^+$ and $Cl^-$ absorption in the rabbit ileum by interacting with $D_2$ and $\alpha_2$-adrenergic receptors. Dopamine also has other effects on $Na^+$ metabolism. In CF, the epithelial $Na^+$ channel (ENaC) is highly active, leading to excess $Na^+$ absorption. Helms et al. found that dopamine increases ENaC activity in a rat alveolar type 2 cell line L2 through the $D_1$ receptor, and in alveolar type I (AT1) cells through $D_1$, but not $D_2$ dopamine receptors.

Spiperone also is a known antagonist to the serotonin 5-$HT_2$ receptor ($IC_{50}$ of 40 nM), which affects the release and activity of other neurotransmitters such as glutamate, GABA, and, as part of this complex net, dopamine. The receptor ligand, 5-HT, is particularly important as a well known mediator of intestinal $Cl^-$ secretion. Exogenous 5-HT is known to induce $Cl^-$ secretion that is inhibited by the cyclooxygenase inhibitor piroxicam in the rat distal colon. The 5-$HT_3$ receptor agonists also activate $Cl^-$ secretion in the rat distal colonic mucosa.

Haloperidol is a potent neuroleptic drug that also binds to dopamine $D_2$ receptors with high affinity. Radiolabelled $^3$H-spiperidone and $^3$H-haloperidol bind selectively and with high affinity to dopamine receptor sites in the mammalian brain and inhibit their functioning. Ketanserin is new 5-$HT_2$ antagonist that binds to the 5-$HT_2$ receptor with a high affinity, similar to that of $^3$H-spiperone. Ketanserin is very weakly antagonistic to the dopamine receptor.

Of these three, it was found that only spiperone could stimulate $Cl^-$ secretion in epithelial cells. Cells responded to spiperone after being pretreated with haloperidol, which suggests that spiperone is not operating as an antagonist of $D_2$ receptors to stimulate $Cl^-$ secretion in human airway epithelia in vitro. The response of the cells to ketanserin also suggested that in this case spiperone does not operate through a 5-$HT_2$ receptor to activate $Cl^-$ secretion.

It should be noted that these results have not been universal, and that the effect of 5-HT on airway epithelium ion transport is still not entirely clear. In another study, results were in the opposite direction: 5-HT inhibited airway epithelial $Na^+$ absorption, stimulated $Cl^-$ secretion in canine tracheal epithelia and spiperone (as well as ketanserin) blocked those effects. In our data, human and mouse airway epithelial cells, spiperone stimulates $Cl^-$ secretion through a $Ca^{2+}$-dependent mechanism. The most likely explanation for the difference may be drug dosing. When spiperone worked as an antagonist of 5-HT receptor in the previous study, its $IC_{50}$ for inhibiting 5-HT-stimulated $Cl^-$ secretion is 0.36 µmol. In our study, at least 1 µmol of the spiperone was required to induce $Cl^-$ secretion. Another reason for the discrepancies may lie in the tissue preparation. In the previous study, dog trachea was excised and mounted on two Lucite half-chambers, whereas we grew human airway epithelial cells in monolayers that were mounted in Ussing chambers.

Spiperone's different responses in these two studies may indicate that a new function for it may have been identified beyond its known role as an antagonist of 5-$HT_2$ and dopamine $D_2$ receptors. Because it apparently has a number of functions in the body, it is likely that it would have to be chemically modified to avoid unintended effects before being developed as a treatment for CF.

In conclusion, a new application has been developed by using the compound screening system to assess cytoplasmic $Ca^{2+}$ change, and the assay has proved its value in our search for a therapeutic compound for CF. It identified a new role for spiperone as an enhancer of cytoplasmic $Ca^{2+}$ that affects CaCC and induces $Cl^-$ secretion in epithelial tissue. Clearly established is that this function of spiperone operates through the PYK-coupled PLC pathway, although its targets have yet to be identified. Spiperone activates $Ca^{2+}$ release and stimulates $Cl^-$ secretion in human airway epithelia by mechanisms other than its well-known function as an antagonist of 5-$HT_2$ and dopamine $D_2$ receptors. Its newly found action on $Cl^-$ transport appears to be separate from its antipsychotic pathway. It rescues CF nasal epithelia in mice by inducing sustained $Cl^-$ secretion.

V. Pharmaceutical Compositions/Methods of Administration

The invention provides a pharmaceutical composition comprising a compound of the invention and a pharmaceutically suitable excipient.

The present invention is also directed to pharmaceutical compositions comprising an effective amount of one or more compounds according to the present invention (including a pharmaceutically acceptable salt, thereof), optionally in combination with a pharmaceutically acceptable carrier, excipient or additive.

A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

The compounds of the present invention may be administered orally, parenterally, by inhalation spray, rectally, vaginally, or topically in dosage unit formulations containing conventional pharmaceutically acceptable carriers, adjuvants, and vehicles. The term parenteral as used herein includes, subcutaneous, intravenous, intramuscular, intrasternal, infusion techniques, intraperitoneally, eye or ocular, intrabuccal, transdermal, intranasal, into the brain, including intracranial and intradural, into the joints, including ankles, knees, hips, shoulders, elbows, wrists, directly into tumors, and the like, and in suppository form.

The pharmaceutically active compounds of this invention can be processed in accordance with conventional methods of pharmacy to produce medicinal agents for administration to patients, including humans and other mammals.

Modifications of the active compound can affect the solubility, bioavailability and rate of metabolism of the active species, thus providing control over the delivery of the active species. Further, the modifications can affect the activity of the compound, in some cases increasing the activity over the parent compound. This can easily be assessed by preparing the derivative and testing its activity according to known methods well within the practioner's skill in the art.

Pharmaceutical compositions based upon these chemical compounds comprise the above-described compounds in a therapeutically effective amount for treating diseases and conditions which have been described herein, optionally in combination with a pharmaceutically acceptable additive, carrier and/or excipient. One of ordinary skill in the art will recognize that a therapeutically effective amount of one or more compounds according to the present invention will vary with the infection or condition to be treated, its severity, the treatment regimen to be employed, the pharmacokinetics of the agent used, as well as the patient (animal or human) treated.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used.

The active compound is included in the pharmaceutically acceptable carrier or diluent in an amount sufficient to deliver to a patient a therapeutically effective amount for the desired indication, without causing serious toxic effects in the patient treated.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

A skilled artisan will recognize that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

The compound may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

It should be understood that in addition to the ingredients particularly mentioned above, the formulations of the present invention may include other agents conventional in the art having regard to the type of formulation in question, for example, those suitable for oral administration may include flavoring agents.

In certain pharmaceceutical dosage forms, the prodrug form of the compounds may be preferred. One of ordinary skill in the art will recognize how to readily modify the present compounds to prodrug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214. The prodrug forms may be active themselves, or may be those such that when metabolized after administration provide the active therapeutic agent in vivo.

Pharmaceutically acceptable salt forms may be the preferred chemical form of compounds according to the present invention for inclusion in pharmaceutical compositions according to the present invention.

Certain of the compounds, in pharmaceutical dosage form, may be used as agents for preventing a disease or condition from manifesting itself. In certain pharmaceutical dosage forms, the prodrug form of the compounds according to the present invention may be preferred. In particular, prodrug forms which rely on $C_1$ to $C_{20}$ ester groups or amide groups (preferably a hydroxyl, free amine or substituted nitrogen group) which may be transformed into, for example, an amide or other group may be particularly useful in this context.

The present compounds or their derivatives, including pro-drug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

Preferred unit dosage formulations are those containing a daily dose or unit, daily sub-dose, as hereinabove recited, or an appropriate fraction thereof, of the administered ingredient.

The dosage regimen for treating a disorder or a disease with the CaCC stimulating compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject will depend on a number of factors, such as the mode of administration, the nature of the condition being treated, the body weight of the subject being treated and the judgment of the prescribing physician.

The amount of compound included within therapeutically active formulations according to the present invention is an effective amount for treating the disorder. In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg/day to about 100 mg/kg/day. The dosage of the compound will depend on the condition being treated, the particular compound, and other clinical factors such as weight and condition of the patient and the route of administration of the compound. It is to be understood that the present invention has application for both human and veterinary use.

The compound is conveniently administered in any suitable unit dosage form, including but not limited to one containing 1 to 3000 mg, preferably 5 to 500 mg of active ingredient per unit dosage form. An oral dosage of 10-250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In certain embodiments, the compound is administered once daily; in other embodiments, the compound is administered twice daily; in yet other embodiments, the compound is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compounds of the invention can be used to treat diseases and disease conditions that are acute, and may also be used for treatment of chronic conditions. In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

In one aspect, the invention provides a pharmaceutical composition comprising a compound of formula I and a pharmaceutically suitable excipient.

In another aspect, the invention provides a kit comprising an effective amount of a compound of formula I in unit dosage form, together with instructions for administering the compound to a subject suffering from or susceptible to a CaCC related disease.

Still other objects, features, and attendant advantages of the present invention will become apparent to those skilled in the art from a reading of the preceding detailed description of embodiments constructed in accordance therewith, taken in conjunction with any accompanying drawings.

The invention will be further described in the following examples. It should be understood that these examples are for illustrative purposes only and are not to be construed as limiting this invention in any manner.

EXAMPLES

Example 1

Cell and Monolayer Culture

Flask Culture: Three cell lines and one primary cell culture were used for this study. IB3-1 is a CF human bronchial epithelial cell line that is heterozygous with two different CFTR mutations ($\Delta$F508 and W1282X). Calu-3 is a non-CF human submucosal gland serous epithelial cell line. CFBE41o- is a CF human bronchial epithelial cell line that is homozygous for ΔF508 mutations. CFBE41o- cell is a gift from Dr. Dieter Gruenert (University of Vermont). NHBE is a normal human bronchial/tracheal epithelial primary cell purchased from Lonza (Walkersville, Md.). In general, IB3-1 cells were cultured in LHC-8 medium (Invitrogen, Carlsbad, Calif.) supplemented with 5% fetal bovine serum (FBS), 100 units/ml penicillin, 100 μg/ml streptomycin, 2 mmol L-glutamine, and 1 μg/ml fungizone. Calu-3 and CFBE41o- cells were cultured in Minimum Essential Medium (Invitrogen, Carlsbad, Calif.) supplemented with 10% FBS, 100 units/ml penicillin, 100 μg/ml streptomycin, 2 mM L-glutamine. NHBE cells were cultured in BEGM medium purchased from Lonza. Culture on Permeable Filter Supports: For the short circuit current measurement, Calu-3 and CFBE41o- cells were cultured in the same medium as the cells in the flask, but on the 12 mm Snapwell Permeable Supports (Costar, Corning, N.Y.). Cell resistance was measured during the culture. The experiments were started when the Calu-3 cells' resistance reached 1500-2000Ω (5-7 days) and CFBE41o-cells' resistance reached 800-1200Ω (3-5 days).

Example 2

Compound Screening for the Calcium Enhancers

Compound Library: Library MSSP (Microsource Discovery Inc) was our source for compounds for the primary screening. The compounds were known bioactive compounds and natural products and their derivatives. The library contained 2,000 compounds on twenty-five 96-well plates, with 80 compounds tested per plate. In the master plates, each compound was suspended in DMSO at a concentration of 10 mM. A set of 96-well plates of the library in a concentration of 2 mM in DMSO was made prior to the screening.

Screening Procedure: The screening was performed by the Johns Hopkins University High Throughput Biology Center Chemcore. The 96-well black plates with transparent bottom were coated with collagen I (Sigma, St. Louis, Mo.) overnight. IB3-1 cells were seeded onto the collagen plates at 50,000 cells per well by a Biotek Multidrop system. Cells were incubated in 37° C., 5% $CO_2$ incubator overnight. At the time of the screening, cells were loaded with Fura-2AM for 2 h and then washed three times with PBS. The fluorescence ratio was measured in ECaT Ringer's solution by a Tecan Safire Fluorescence Plate Reader. Then small molecule compounds (80 compounds per plate) were added by the robotic arm to the cells at the final concentration of 20 μM with zinc as the positive control and DMSO (5%) as the negative control. The fluorescence ratio was measured again immediately after adding the compounds. The final fluorescence detection was done 15 min after the second detection in order to find compounds which stimulate the sustained $Ca^{2+}$ increase.

Example 3

Fura-2 Microscope Calcium Measurement

Cells were seeded on the collagen-coated cover glass for 48 h. Cell $Ca^{2+}$ was measured with a dual excitation wavelength microscope system. Fura-2 fluorescence was excited at 340 nm and 380 nm with xenon light. Fluorescence was measured at 510 nm emission wavelength. Data was processed and analyzed using IPLab 4.0 software. Fluorescence data of each experiment were normalized to the individual basal fluorescence value $\Delta F/F_0 = (F - F_0)/F_0$ to bring all the response curves to the same pretreatment starting point.

Example 4

Short-Circuit Current Measurements

Calu-3 and CFBE41o-cells were cultured on Snapwell inserts until they formed a tight monolayer as monitored by measuring the transepithelial resistance. The bottom of the monolayer was taken out, mounted on the Ussing chamber and buffered by the testing solutions. The short-circuit current was measured by a VCC MC6 multichannel voltage/current clamp (Physiologic Instruments, San Diego, Calif.). Data were recorded and analyzed by Acquire and Analyze software.

Example 5

Mouse Nasal Potential Difference Measurements

Animals: The studies conducted were approved by the Johns Hopkins University Animal Care and Use Committee. The double transgenic CFKO ($CFTR^{tm1Unc}$-Tg (FAB-PCFTR) 1Jaw/J) mice were bred at the Johns Hopkins University Animal Core Facility (JAX #002364). Wild-type C57B1/6 (JAX #000664) strains of female mice were obtained from JAX Mice (Bar Harbor, Mass.). Nasal Potential Difference (NPD): All mice were anesthetized with an IP injection of a ketamine and xylazine mixture (100 mcg/10 mcg per gram of body weight). NPD measurements were undertaken using a modification of methods described by Grubb et al (Am J. Physiol Lung Cell Mol Physiol 290: L270-L277, 2006). Briefly, a high impedance voltmeter (World Precision Instruments, Sarasota, Fla.) was connected by silver-chloride pellet electrodes to an exploring nasal bridge and a reference subcutaneous bridge. The nasal bridge, a single polyethylene tube (PE10, 0.28 mm ID, Clay-Adams, B D, Sparks, Md.) was pulled to one-half its original diameter and cut at a 45 degree angle. The tubing was marked and inserted 5 mm from the tip of the nare. A paper tape flag indicated position and orientation of the tip. The subcutaneous bridge was a 25 GA Butterfly® (Abbott, Chicago, Ill.) needle containing Ringer's solution inserted subcutaneously in the right abdominal wall. Each solution was warmed to 37° C. and perfused to the nare for at least 3 minutes at 5 micro liters per minute using a perfusion pump. Following the procedure, the oral cavity was gently suctioned of perfusate and the mice were recovered to their cages. Voltmeter data (mV) was recorded by a PowerLab A/D converter connected to a PC running Chart software at 20 samples per second (AD Instruments, Colorado Springs, Colo.). A minimum of 400 data points (~20 seconds) were used to calculate the mean voltage values.

Data Analysis.

Data are present as means±SE. All data were analyzed by paired t-test or one-way ANOVA with Tukey post-hoc multiple comparisons using GraphPad prism software. Significance was set at $p < 0.05$.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

A number of embodiments of the invention have been described. Embodiments herein include those recited alone or in combination with other delineated embodiments herein. Nevertheless, it will be understood that various modifications may be made without departing from the spirit and scope of the invention. Accordingly, other embodiments are within the scope of the following claims.

What is claimed:
1. A method of treating cystic fibrosis in a subject in need thereof, the method comprising the steps of administering to the subject an effective amount of a compound selected from the group consisting of:
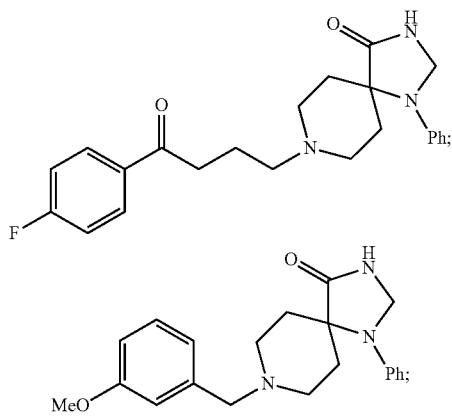
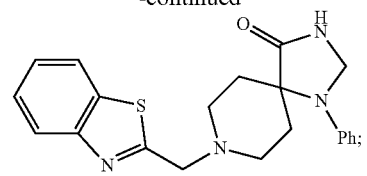
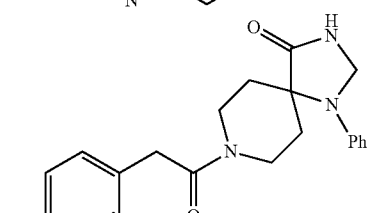 and
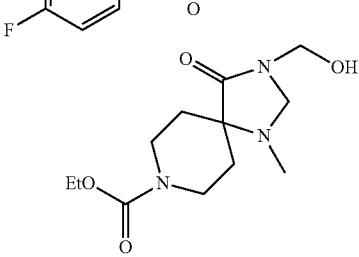
or a pharmaceutically acceptable salt thereof.
* * * * *